(12) United States Patent
Fukumoto et al.

(10) Patent No.: US 8,541,606 B2
(45) Date of Patent: Sep. 24, 2013

(54) TERTIARY ALCOHOL DERIVATIVE, POLYMER COMPOUND AND PHOTORESIST COMPOSITION

(75) Inventors: Takashi Fukumoto, Niigata (JP); Ichihiro Aratani, Niigata (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 13/328,730

(22) Filed: Dec. 16, 2011

(65) Prior Publication Data

US 2012/0149921 A1 Jun. 14, 2012

Related U.S. Application Data

(62) Division of application No. 12/279,774, filed as application No. PCT/JP2007/052892 on Feb. 16, 2007, now Pat. No. 8,105,746.

(30) Foreign Application Priority Data

Feb. 17, 2006 (JP) .................................. 2006 041402

(51) Int. Cl.
*C07D 307/26* (2006.01)

(52) U.S. Cl.
USPC ............ 549/320; 549/323; 549/200; 549/263

(58) Field of Classification Search
USPC ................... 549/320, 323, 200, 263
See application file for complete search history.

(56) References Cited

U.S. PATENT DOCUMENTS

| | | | |
|---|---|---|---|
| 4,188,472 | A | 2/1980 | Chang |
| 5,696,212 | A | 12/1997 | Isozaki |
| 6,291,130 | B1 | 9/2001 | Kodama et al. |
| 7,037,995 | B2 | 5/2006 | Watanabe et al. |
| 7,316,884 | B2 | 1/2008 | Ansai et al. |
| 8,105,746 | B2 * | 1/2012 | Fukumoto et al. ......... 430/270.1 |
| 2004/0024228 | A1 | 2/2004 | Ishii et al. |
| 2004/0058269 | A1 | 3/2004 | Hada et al. |

FOREIGN PATENT DOCUMENTS

| | | |
|---|---|---|
| DE | 19835533 A1 | 2/2000 |
| EP | 1 480 079 A2 | 11/2004 |
| EP | 1 480 079 A3 | 11/2004 |
| EP | 1 480 079 A8 | 11/2004 |
| JP | 61063675 A | 4/1986 |
| JP | 9 73173 | 3/1997 |
| JP | 11 223950 | 8/1999 |
| JP | 2000 267287 | 9/2000 |
| JP | 2003 167347 | 6/2003 |
| JP | 2004 046206 | 2/2004 |
| JP | 2004 46206 | 2/2004 |
| JP | 2004 175981 | 6/2004 |
| JP | 2006 18071 | 1/2006 |
| WO | 02 06262 | 1/2002 |

OTHER PUBLICATIONS

Machine translation of JP2000-267287 (no date).
Helga Marschall, et al., "Synthesis of Hydroxy-γ-lactones from α, β-Unsaturated Aldehydes," Liebigs Annalen Der Chemie, XP-002545397, 1982, pp. 49-67, with English Abstract.

* cited by examiner

*Primary Examiner* — Amanda C. Walke
(74) *Attorney, Agent, or Firm* — Oblon, Spivak, McClelland, Maier & Neustadt, L.L.P.

(57) ABSTRACT

A polymer compound for a photoresist composition (a) having a high dissolution rate in a developing solution after exposure and (b) exhibiting little swelling during development. A tertiary alcohol derivative that is a raw material for the polymer compound. A tertiary alcohol that is an intermediate of the tertiary alcohol derivative. The tertiary alcohol is represented by formula (3):

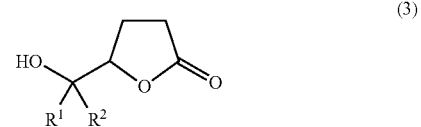

(3)

wherein $R^1$ and $R^2$ individually represent a linear, branched or cyclic alkylene group having 2 to 9 carbon atoms, which may contain an oxygen atom, and wherein $R^1$ and $R^2$ may together form a ring with a carbon atom to which $R^1$ and $R^2$ are bonded.

13 Claims, No Drawings

TERTIARY ALCOHOL DERIVATIVE, POLYMER COMPOUND AND PHOTORESIST COMPOSITION

CROSS-REFERENCE TO RELATED APPLICATIONS

This application is a divisional of U.S. patent application Ser. No. 12/279,774 filed Aug. 18, 2008 which is a National Stage of PCT/JP07/52892 filed Feb. 16, 2007 and claims priority from Japanese Patent Application No. 2006 041402 filed Feb. 17, 2006.

TECHNICAL FIELD

The present invention relates to a novel tertiary alcohol derivative and a method for manufacturing the same. The tertiary alcohol derivative obtained by the present invention is useful as a raw material compound of a polymer compound obtained by polymerizing at least the subject tertiary alcohol derivative as one of raw materials and of a photoresist composition containing the subject polymer compound as a component.

BACKGROUND ART

In recent years, in the electronic device manufacture field represented by the manufacture of integrated circuit devices, a demand for high integration of devices is increasing, and therefore, a photolithography technology for forming a fine pattern is considered to be necessary. For that reason, the development of a photoresist composition adaptive with photolithography using, as exposure light, radiations having a wavelength of not more than 220 nm, for example, an ArF excimer laser (wavelength: 193 nm), an $F_2$ excimer laser (wavelength: 157 nm), etc. is desired, and there have been proposed a number of photoresist compositions of a chemical amplification type composed of an acid dissociable functional group-containing polymer compound and a compound capable of generating an acid upon irradiation with radiations (hereinafter referred to as "exposure") (the latter compound will be hereinafter referred to as "photo acid generator"). For example, there are known photoresist compositions containing, as a component, a polymer compound having an adamantyl group-containing acrylic ester as a constitutional unit as the acid dissociable functional group-containing polymer compound (see Non-Patent Document 1 and Patent Document 1); and photoresist compositions containing, as a component, a polymer compound having a lactone ring-containing constitutional unit as the acid dissociable functional group-containing polymer compound (see Patent Document 2).

Non-Patent Document 1: *Journal of Photopolymer Science and Technology*, Vol. 9, No. 3, 475 to 487 (1996)
Patent Document 1: JP-A-9-73173
Patent Document 2: JP-A-2004-46206

DISCLOSURE OF THE INVENTION

Problems that the Invention is to Solve

In recent years, under the circumstances that much more fine fabrication of a pattern rule in electronic devices is demanded, photoresist compositions containing, as a component, a polymer compound having a lactone based protective group-containing constitutional unit, which are improved in sensitivity, resolution, dry etching resistance, etc. were proposed (see Patent Documents 3 and 4). However, it is the present situation that it is hard to say that these photoresist compositions have sufficient performance. The most serious problem is line width fluctuation of a pattern to be formed, which is called "line width roughness" (LWR), and it is required that its tolerable value is less than 8% of the line width (see Non-Patent Document 2). In order to improve LWR, it is necessary that pattern deformation to be caused due to swelling is suppressed. In order to suppress the pattern deformation to be caused due to swelling, it is necessary that the polymer compound which is the photoresist composition component is hardly swollen. However, in polymer compounds prepared through a combination of polymerizable compounds which have hitherto been known, those having a performance on a satisfactory level are not always obtained. For that reason, the development of a polymer compound for photoresist composition which is more hardly swollen is still desired earnestly.

Patent Document 3: JP-A-11-223950
Patent Document 4: JP-A-2000-267287
Non-Patent Document 2: *International Technology Roadmap for Semiconductors (ITRS)* 2006, "Lithography", page 7

As a result of extensive and intensive investigations regarding a lactone based protective group-containing polymer compound to be used for a photoresist composition of a chemical amplification type for the purpose of solving the foregoing problems of the background art, the present invention has been made. Its object is to provide (1) a polymer compound for photoresist composition which is small swelling at the development and (2) a polymerizable compound which is a raw material for such a polymer compound; and further to provide (3) a photoresist composition with improved LWR comprising the subject polymer compound.

The present inventors made extensive and intensive investigations regarding a relationship between properties of a polymer compound for photoresist composition and swelling properties of a photoresist composition using it as a component at the development. As a result, the present inventors have found out that when a polymer compound for photoresist composition having a high dissolution rate to a developing solution after exposure is used, swelling can be suppressed. Furthermore, the present inventors have found a polymer compound having a specified structure as the polymer compound for photoresist components having a high dissolution rate to a developing solution after exposure and a polymerizable compound which is a raw material for such a polymer compound, leading to accomplishment of the invention.

Means for Solving the Problems

According to the present invention, the foregoing problems have been achieved by providing:
1. A tertiary alcohol derivative represented by the following general formula (1) (hereinafter referred to as "tertiary alcohol derivative (1)"):

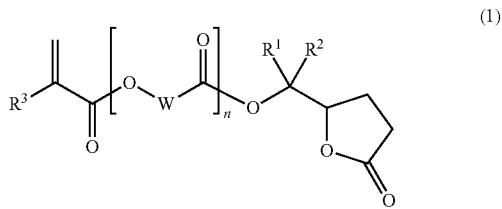

(in the formula, $R^1$ and $R^2$ are taken together to form a ring together with a carbon atom to which $R^1$ and $R^2$ are bonded, and $R^1$ and $R^2$ as taken represent a linear, branched or cyclic alkylene group having from 2 to 9 carbon atoms, which may contain an oxygen atom at an arbitrary position; $R^3$ represents a hydrogen atom or a methyl group; W represents a linear, branched or cyclic alkylene group having from 1 to 10 carbon atoms; and n represents 0 or 1);

2. The tertiary alcohol derivative (1), wherein W is a methylene group or an ethane-1,1-diyl group;
3. The tertiary alcohol derivative (1), wherein n is 0;
4. A method for manufacturing the tertiary alcohol derivative (1) comprising, as a first step, oxidizing a carboxylic acid derivative represented by the following general formula (2) (hereinafter referred to as "carboxylic acid derivative (2)"):

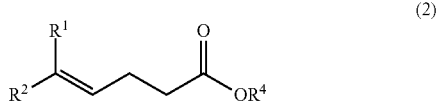

(2)

(in the formula, $R^1$ and $R^2$ are the same as defined above; and $R^4$ represents an alkyl group having from 1 to 10 carbon atoms, an aryl group having from 6 to 12 carbon atoms or an aralkyl group having from 7 to 13 carbon atoms) in the presence of a water, or oxidizing a carboxylic acid derivative represented by the following general formula (2') (hereinafter referred to as "carboxylic acid derivative (2')"):

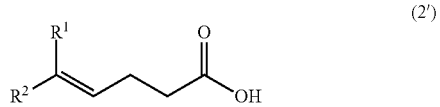

(2')

(in the formula, $R^1$ and $R^2$ are the same as defined above), thereby obtaining a tertiary alcohol represented by the following general formula (3) (hereinafter referred to as "tertiary alcohol (3)"):

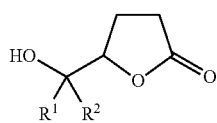

(3)

(in the formula, $R^1$ and $R^2$ are the same as defined above); and, as a second step, subsequently allowing the tertiary alcohol (3) to react with a polymerizable group introducing agent, or allowing the tertiary alcohol (3) to react with a connecting group introducing agent and then to react with a polymerizable group introducing group;
5. A method for manufacturing the tertiary alcohol (3) comprising oxidizing the carboxylic acid derivative (2) in the presence of water or oxidizing the carboxylic acid derivative (2');
6. The tertiary alcohol (3);
7. A polymer compound obtained by polymerizing at least the tertiary alcohol derivative (1) as one of raw materials (this polymer compound will be hereinafter referred to as "polymer compound (4)"); and
8. A photoresist composition comprising the polymer compound (4) and a photo acid generator.

Advantages of the Invention

According to the present invention, it is possible to provide (1) a polymer compound for photoresist composition which has a high dissolution rate to a developing solution after exposure and which is small swelling at the development and (2) a polymerizable compound which is a raw material of the subject polymer compound; and it is also possible to provide (3) a photoresist composition containing the subject polymer compound, which is improved in LWR.

BEST MODES FOR CARRYING OUT THE INVENTION

In the foregoing formulae, examples of the linear, branched or cyclic alkylene group having from 2 to 9 carbon atoms, which is represented by $R^1$ and $R^2$ as taken and which may contain an oxygen atom at an arbitrary position, include a 1,2-ethanediyl group, a 1,3-propanediyl group, a 1,4-butanediyl group, a 1,5-pentanediyl group, a 1,6-hexanediyl group, a (cyclopentane-1',3'-diyl)methyl group, a (2',2',3'-trimethylcyclopentane-1',3'-diyl)methyl group, a bicyclo[3,3,1]nonane-3,7-diyl group, a 2-oxabutane-1,4-diyl group, a 2-oxapentane-1,5-diyl group and a 3-oxopentane-1,5-diyl group. Examples of the ring structure having from 3 to 10 carbon atoms, which is formed by $R^1$ and $R^2$ together with a carbon atom to which $R^1$ and $R^2$ are bonded and which may contain an oxygen atom at an arbitrary position, include a cyclopropane ring, a cyclobutane ring, a cyclopentane ring, a cyclohexane ring, a cycloheptane ring, a camphor ring, a norbornane ring, an adamantane ring, a tetrahydrofuran ring and a tetrahydropyran ring.

Examples of the linear, branched or cyclic alkylene group having from 1 to 10 carbon atoms represented by W of the tertiary alcohol derivative (1) include a methylene group, an ethane-1,1-diyl group, an ethane-1,2-diyl group, a propane-1,1-diyl group, a propane-1,2-diyl group, a propane-1,3-diyl group, a pentane-1,5-diyl group, a hexane-1,1-diyl group and a cyclohexane-1,4-diyl group. Of these, a methylene group and an ethane-1,1-diyl group are preferable.

Examples of the alkyl group represented by $R^4$ of the ester compound (2) include an ethyl group and a methyl group; examples of the aryl group include a phenyl group; and examples of the aralkyl group include a benzyl group.

n of the tertiary alcohol derivative (1) is 0 or 1, with 0 being preferable.

Specific examples of the tertiary alcohol derivative (1) include the following formulae (1-a) to (1-l), but it should not be construed that the present invention is limited thereto:

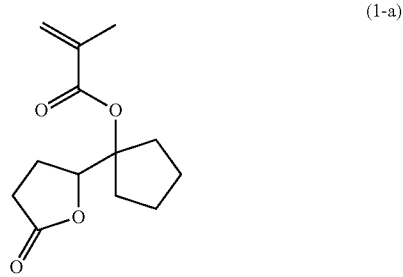

(1-a)

(1-b)
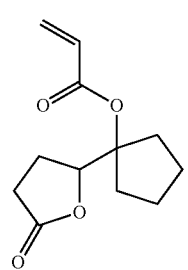
(1-c)
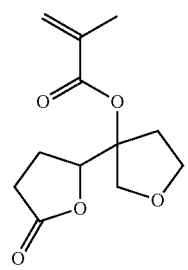
(1-d)
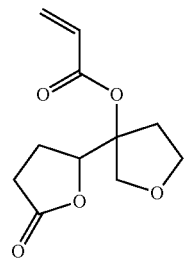
(1-e)
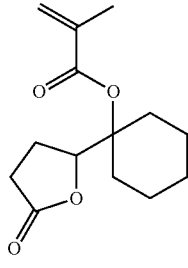
(1-f)
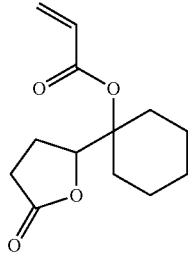
(1-g)
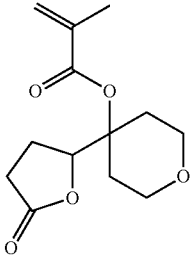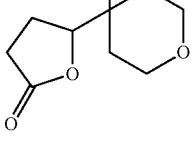
(1-h)
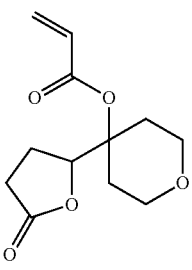
(i-i)
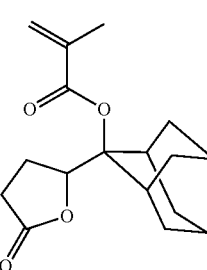
(i-j)
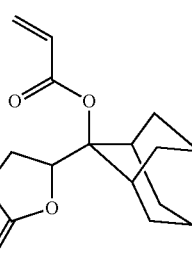
(1-k)
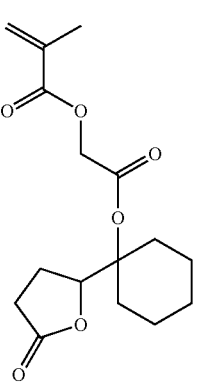
(1-l)
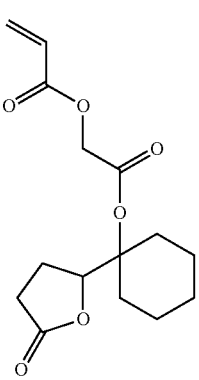
The tertiary alcohol derivative (1) can be, for example, manufactured by the following process, but it should not be construed that the present invention is limited thereto.

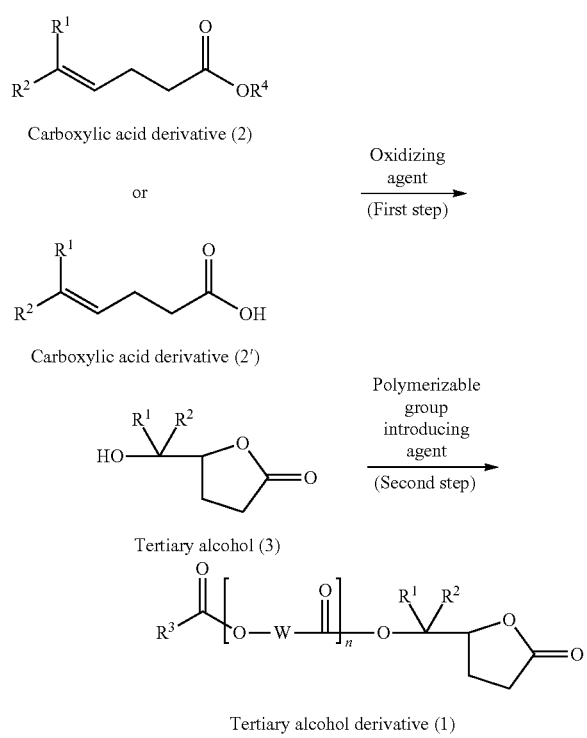

Carboxylic acid derivative (2)

or

Carboxylic acid derivative (2')

Tertiary alcohol (3)

Tertiary alcohol derivative (1)

(In the formulae, $R^1$, $R^2$, $R^3$ and $R^4$ are the same as defined.)

The respective steps are hereunder described.

A method for manufacturing the carboxylic acid derivative (2) or carboxylic acid derivative (2') to be used in the first step is not particularly limited. The carboxylic acid derivative (2) can be, for example, manufactured by the Johnson-Claisen rearrangement reaction between a corresponding allyl alcohol and a corresponding trialkyl orthoacetate, triaryl orthoacetate or triaralkyl orthoacetate in the presence of an acid catalyst. The carboxylic acid derivative (2') can be, for example, manufactured by oxidation of a corresponding alcohol or hydrolysis of the carboxylic acid derivative (2) which can be manufactured by the foregoing method.

Examples of the oxidizing agent to be used in the first step include percarboxylic acids, for example, performic acid, peracetic acid, m-chloroperbenzoic acid, etc.; metal peroxides obtained by allowing sodium tungstenate, vanadium oxide, etc. to react with hydrogen peroxide, t-butylhydroperoxide, etc.; and osmium tetroxide. Above all, it is the most preferable that performic acid is formed in a system from formic acid and hydrogen peroxide and used. From the viewpoints of economy and easiness of post-treatment, the use amount of the oxidizing agent is preferably in the range of from 0.8 times by mole to 10 times by mole, and more preferably in the range of from 1 time by mole to 2 times by mole relative to the carboxylic acid derivative (2) or carboxylic acid derivative (2').

In case of using the carboxylic acid derivative (2), the first step is carried out in the presence of water. The use amount of water is sufficient to be 1 time by mole or more relative to the carboxylic acid derivative (2). In case of using the carboxylic acid derivative (2'), the first step can be carried out in the presence or absence of water.

The first step can be carried out in the presence or absence of a solvent. The solvent is not particularly limited so far as it does not hinder the reaction, and examples thereof include water; aliphatic hydrocarbons, for example, hexane, heptane, octane, etc.; aromatic hydrocarbons, for example, toluene, xylene, cymene, etc.; halogenated hydrocarbons, for example, methylene chloride, dichloroethane, etc.; ethers, for example, tetrahydrofuran, diisopropyl ether, etc.; and carboxylic acids, for example, formic acid, acetic acid, etc. These solvents may be used singly or may be used in admixture of two or more kinds thereof. In case of using a solvent, from the viewpoints of economy and easiness of post-treatment, the use amount thereof is preferably in the range of from 0.1 times by mass to 10 times by mass, and more preferably in the range of from 0.1 times by mass to 5 times by mass relative to the carboxylic acid derivative (2) or carboxylic acid derivative (2').

A reaction temperature of the first step varies depending upon the kind of each of the carboxylic acid derivative (2) or carboxylic acid derivative (2') and the oxidizing agent to be used, and in general, it is preferably in the range of from −40° C. to 100° C.

The reaction time of the first step varies depending upon the carboxylic acid derivative (2) or carboxylic acid derivative (2') and the oxidizing agent to be used and the reaction temperature, and in general, it is preferably in the range of from 0.5 hours to 48 hours, and more preferably in the range of from 1 hour to 24 hours.

The reaction of the first step can be terminated by adding a reducing agent. Examples of the reducing agent include sulfites, for example, sodium sulfite, sodium hydrogensulfite, etc.; and sulfides, for example, dimethyl sulfide, diphenyl sulfide, etc. The use amount of the reducing agent is preferably in the range of from 1 equivalent to 5 equivalents to the excess of the oxidizing agent.

The thus obtained tertiary alcohol (3) can be isolated by an operation which is usually employed in isolating an organic compound, for example, solvent extraction, distillation, column chromatography, recrystallization, etc.

The thus obtained tertiary alcohol (3) is a novel compound.

Next, the second step is described.

In the case where n of the tertiary alcohol derivative (1) is 0, the second step is carried out by allowing the tertiary alcohol (3) as obtained in the first step to react with a compound represented by a formula: $CH_2=CR^3COX$ (in the formula, $R^3$ is the same as defined above); a formula: $(CH_2=CR^3CO)_2O$ (in the formula, $R^3$ is the same as defined above); a formula: $CH_2=CR^3COOC(=O)R^5$ (in the formula, $R^3$ is the same as defined above; and $R^5$ represents a t-butyl group or a 2,4,6-trichlorophenyl group); or a formula: $CH_2=CR^3COOSO_2R^6$ (in the formula, $R^3$ is the same as defined above; and $R^6$ represents a methyl group or a p-tolyl group) (such a compound will be hereinafter referred to "polymerizable group introducing agent A") in the presence of a basic substance (this reaction step will be hereinafter referred to as "second step A"). In the case where n of the tertiary alcohol derivative (1) is 1, the second step is carried out by allowing the tertiary alcohol (3) obtained in the first step to react with a compound represented by a formula: X—W—COX (in the formula, W is the same as defined above; and X represents a chlorine atom, a bromine atom or an iodine atom); a formula: $(X-W-C(=O))_2O$ (in the formula, W and X are the same as defined above); a formula: X—W—COOC(=O)$R^7$ (in the formula, X and W are the same as defined above; and $R^7$ represents a t-butyl group or a 2,4,6-trichlorophenyl group); or a formula: X—W—COOSO$_2R^8$ (in the formula, X and W are the same as defined above; and $R^8$ represents a methyl group or a p-tolyl group) (such a compound will be hereinafter referred to "connecting group introducing agent B1") in the presence of a basic substance (this reaction step will be hereinafter "second step B-1"); and subsequently allowing a reaction product to react with a compound represented by a formula: $CH_2=CR^3COOM$ (in the formula, $R^3$ is the same as defined above; and M represents a sodium atom or a potassium atom) (such a compound will be hereinafter referred to "polymerizable group introducing agent B2") (this reaction step will be hereinafter referred to as "second step B-2"). The second step A to second step B are hereunder successively described.

Specific examples of the tertiary alcohol derivative (1) wherein n is 0, which is manufactured by the second step A, include (1-a) to (1-j).

As to the polymerizable group introducing agent A to be used in the second step A, specific examples of the compound represented by the formula: $CH_2=CR^3COX$ include acryloyl chloride and methacryloyl chloride; specific examples of the compound represented by the formula: $(CH_2=CR^3CO)_2O$ include acrylic anhydride and methacrylic anhydride; specific examples of the compound represented by the formula: $CH_2=CR^3COOC(=O)R^5$ include acrylic pivalic anhydride, acrylic 2,4,6-trichlorobenzoic anhydride, methacrylic pivalic anhydride and methacrylic 2,4,6-trichlorobenzoic anhydride; and specific examples of the compound represented by the formula: $CH_2=CR^3COOSO_2R^6$ include acrylic methanesulfonic anhydride, acrylic p-toluenesulfonic anhydride, methacrylic methanesulfonic anhydride and methacrylic p-toluenesulfonic anhydride. From the viewpoints of economy and easiness of post-treatment, the use amount of the polymerizable group introducing agent A is preferably in the range of from 0.8 times by mole to 5 times by mole, and more preferably in the range of from 0.8 times by mole to 3 times by mole relative to the tertiary alcohol (3).

Examples of the basic substance to be used in the second step A include sodium hydride, potassium hydride, sodium hydroxide, potassium hydroxide, sodium carbonate, potassium carbonate, triethylamine, pyridine, tributylamine and diazabicyclo[2,2,2]octane. From the viewpoints of economy and easiness of post-treatment, the use amount of the basic substance is preferably in the range of from 0.8 times by mole to 5 times by mole, and more preferably in the range of from 0.8 times by mole to 3 times by mole relative to the tertiary alcohol (3).

The second step A can be carried out in the presence or absence of a solvent. Though the solvent is not particularly limited so far as it does not hinder the reaction, aliphatic hydrocarbons, for example, hexane, heptane, octane, etc.; aromatic hydrocarbons, for example, toluene, xylene, cymene, etc.; halogenated hydrocarbons, for example, methylene chloride, dichloroethane, etc.; ethers, for example, tetrahydrofuran, diisopropyl ether, etc.; and nitriles, for example, acetonitrile, benzonitrile, etc. are favorable. These solvents may be used singly or may be used in admixture of two or more kinds thereof. In case of using a solvent, from the viewpoints of economy and easiness of post-treatment, the use amount thereof is preferably in the range of from 0.1 times by mass to 10 times by mass, and more preferably in the range of from 0.1 times by mass to 5 times by mass relative to the tertiary alcohol (3).

A reaction temperature of the second step A varies depending upon the kind of each of the polymerizable group introducing agent A, the tertiary alcohol (3) and the basic substance to be used, and in general, it is preferably in the range of from −50° C. to 80° C.

The reaction time of the second step A varies depending upon each of the polymerizable group introducing agent A, the tertiary alcohol (3) and the basic substance to be used and the reaction temperature, and in general, it is preferably in the range of from 0.5 hours to 48 hours, and more preferably in the range of from 1 hour to 24 hours.

The reaction of the second step A can be terminated by adding water or an alcohol. Examples of the alcohol include methanol, ethanol, n-propanol and i-propanol. A mixture of water and an alcohol can also be used. The use amount of water or the alcohol may be one time by mole or more relative to the excess of the polymerizable group introducing agent A. When the use amount is small, there may be the case where the excess of the polymerizable group introducing agent A cannot be completely decomposed, thereby forming a by-product.

Next, the second step B is described. Specific examples of the tertiary alcohol derivative (1) wherein n is 1, which is manufactured by the second step B, include (1-k) to (1-l).

As to the connecting group introducing agent B1 to be used in the second step B-1, specific examples of the compound represented by the general formula: X—W—COX include chloroacetyl chloride, 2-chloropropionyl chloride and 2-bromo-2-methylpropionic acid bromide; specific examples of the compound represented by the formula: X—W—COOC(=O)$R^7$ include chloroacetic acid pivalic anhydride, chloroacetic acid 2,4,6-trichlorobenzoic anhydride, 2-chloropropionic acid pivalic anhydride and 2-chloropropionic acid 2,4,6-trichlorobenzoic anhydride; specific examples of the compound represented by the formula: X—W—COOSO$_2$$R^8$ include chloroacetic acid methanesulfonic anhydride, chloroacetic acid p-toluenesulfonic anhydride, 2-chloropropionic acid methanesulfonic anhydride and 2-chloropropionic acid p-toluenesulfonic anhydride; and specific examples of the compound represented by the formula: (X—W—C(=O))$_2$O include chloroacetic anhydride and 2-chloropropinic anhydride. From the viewpoints of economy and easiness of post-treatment, the use amount of the connecting group introducing agent B1 is preferably in the range of from 0.8 times by mole to 5 times by mole, and more preferably in the range of from 0.8 times by mole to 3 times by mole relative to the tertiary alcohol (3).

Examples of the basic substance to be used in the second step B-1 include sodium hydride, potassium hydride, sodium hydroxide, potassium hydroxide, sodium carbonate, potassium carbonate, triethylamine, pyridine, tributylamine and diazabicyclo[2,2,2]octane. From the viewpoints of economy and easiness of post-treatment, the use amount of the basic substance is preferably in the range of from 0.8 times by mole to 5 times by mole, and more preferably in the range of from 0.8 times by mole to 3 times by mole relative to the tertiary alcohol (3).

The second step B-1 can be carried out in the presence or absence of a solvent. Though the solvent is not particularly limited so far as it does not hinder the reaction, aliphatic hydrocarbons, for example, hexane, heptane, octane, etc.; aromatic hydrocarbons, for example, toluene, xylene, cymene, etc.; halogenated hydrocarbons, for example, methylene chloride, dichloroethane, etc.; ethers, for example, tetrahydrofuran, diisopropyl ether, etc.; and nitriles, for example, acetonitrile, benzonitrile, etc. are favorable. These solvents may be used singly or may be used in admixture of two or more kinds thereof. In case of using a solvent, from the viewpoints of economy and easiness of post-treatment, the use amount thereof is preferably in the range of from 0.1 times by mass to 10 times by mass, and more preferably in the range of from 0.1 times by mass to 5 times by mass relative to the tertiary alcohol (3).

A reaction temperature of the second step B-1 varies depending upon the kind of each of the connecting group introducing agent B1, the tertiary alcohol (3) and the basic substance to be used, and in general, it is preferably in the range of from −50° C. to 80° C.

The reaction time of the second step B-1 varies depending upon the kind of each of the connecting group introducing agent B1, the tertiary alcohol (3) and the basic substance to be used and the reaction temperature, and in general, it is preferably in the range of from 0.5 hours to 48 hours, and more preferably in the range of from 1 hour to 24 hours.

The reaction of the second step B-1 can be terminated by adding water or an alcohol. Examples of the alcohol include methanol, ethanol, n-propanol and i-propanol. A mixture of water and an alcohol can also be used. The use amount of water or the alcohol may be one time by mole or more relative to the excess of the connecting group introducing agent B1. When the use amount is small, there may be the case where the excess of the connecting group introducing agent B1 cannot be completely decomposed, thereby forming a by-product.

An intermediate obtained in the second step B-1 can be used in the second step B-2 upon being isolated from the reaction mixed solution or as the reaction mixed solution stands. In case of isolation from the reaction mixed solution, a method which is usually employed as an isolation method of an organic compound can be employed.

Specific examples of the polymerizable group introducing agent B2 to be used in the second step B-2 include sodium acrylate, potassium acrylate, sodium methacrylate and potassium methacrylate. As the polymerizable group introducing agent B2, a commercially available material can also be used; and a mixture prepared by mixing acrylic acid or methacrylic acid and potassium carbonate, sodium carbonate, potassium hydroxide or sodium hydroxide in the reaction solution can be used, too. Of these, it is preferable to use a mixture prepared in the reaction mixture. From the viewpoints of economy and easiness of post-treatment, the use amount of the polymerizable group introducing agent B2 is preferably in the range of from 0.8 times by mole to 5 times by mole, and more preferably in the range of from 0.8 times by mole to 3 times by mole relative to the intermediate obtained in the second step B-1.

In the second step B-2, it is preferable that, for example, potassium iodide, sodium iodide, tetrabutylammonium iodide, tetrabutylammonium bromide or the like is used as an activating agent as the need arises. In case of using an activating agent, the use amount thereof is preferably in the range of from 0.001 times by mole to 0.5 times by mole relative to the intermediate obtained in the second step B-1, and from the viewpoints of economy and easiness of post-treatment, it is more preferably in the range of from 0.005 times by mole to 0.3 times by mole.

The second step B-2 can be carried out in the presence or absence of a solvent. The solvent is not particularly limited so far as it does not hinder the reaction, and examples thereof include aliphatic hydrocarbons, for example, hexane, heptane, octane, etc.; aromatic hydrocarbons, for example, toluene, xylene, cymene, etc.; halogenated hydrocarbons, for example, methylene chloride, dichloroethane, etc.; ethers, for example, tetrahydrofuran, diisopropyl ether, etc.; and amides, for example, N,N-dimethylformamide, N,N-dimethylacetamide, N-methylpyrrolidone, etc. These solvents may be used singly or may be used in admixture of two or more kinds thereof. In case of using a solvent, from the viewpoints of economy and easiness of post-treatment, the use amount thereof is preferably in the range of from 0.1 times by mass to 10 times by mass, and more preferably in the range of from 0.1 times by mass to 5 times by mass relative to the intermediate obtained in the second step B-1.

A reaction temperature of the second step B-2 varies depending upon the kind of each of the polymerizable group introducing agent B2 to be used and the intermediate obtained in the second step B-1, and in general, it is preferably in the range of from −50° C. to 80° C.

The reaction time of the second step B-2 varies depending upon the kind of each of the polymerizable group introducing agent B2 to be used and the intermediate obtained in the second step B-1 and the reaction temperature, and in general, it is preferably in the range of from 0.5 hours to 48 hours, and more preferably in the range of from 1 hour to 24 hours.

It is preferable that the tertiary alcohol derivative (1) obtained through the second step A or the second step B-1 and second step B-2 is separated and purified in the usual way as the need arises. For example, after washing with water, the reaction mixture can be purified by a method which is employed for usual separation and purification of an organic compound, for example, concentration, distillation, column chromatography, recrystallization, etc. Also, it is possible to reduce the content of a metal in the obtained tertiary alcohol derivative (1) by filtration after addition of a chelating agent, for example, nitrilotriacetic acid, ethylenediaminetetraacetic acid, etc.; or a treatment by a metal removal filter, for example, ZETA PLUS (a trade name, manufactured by CUNO Incorporated), PROTEGO (a trade name, manufactured by Nippon Mykrolis K.K.), etc. as the need arises.

The polymer compound (4) of the present invention is a polymer compound obtained by homopolymerizing the tertiary alcohol derivative (1) or a polymer compound obtained by copolymerizing the tertiary alcohol derivative (1) and other polymerizable compound. In case of a copolymer, it contains a constitutional unit on the basis of the tertiary alcohol derivative (1) in an amount preferably in the range of from 10 to 80% by mole, and more preferably in the range of from 20 to 70% by mole. Specific examples of the constitutional unit on the basis of the tertiary alcohol derivative (1) include those represented by the following formulae (1'-a) to (1'-l), but it should not be construed that the present invention is limited thereto.

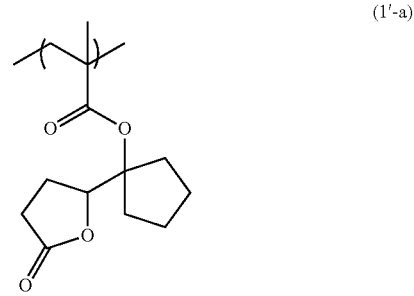

(1'-a)

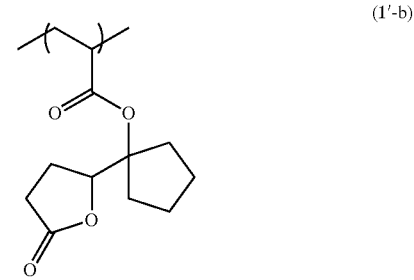

(1'-b)

-continued
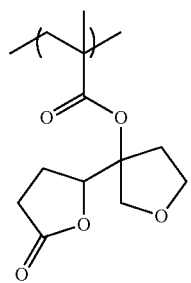
(1′-c)
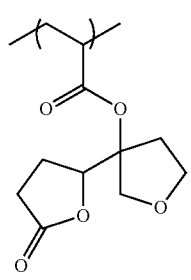
(1′-d)
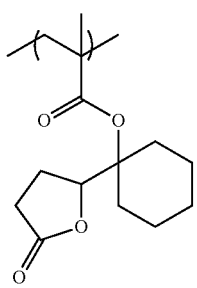
(1′-e)
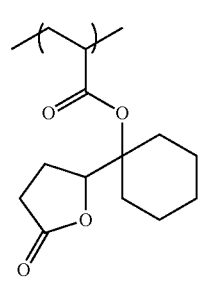
(1′-f)
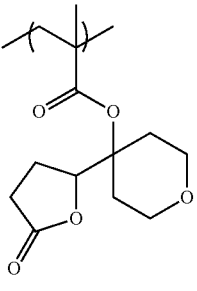
(1′-g)
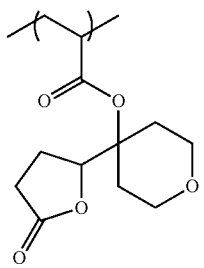
(1′-h)
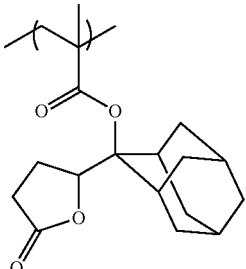
(1′-i)
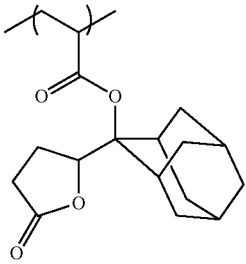
(1′-j)
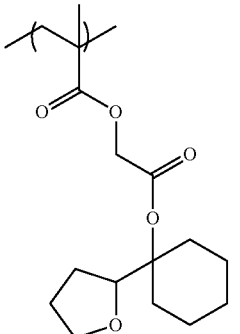
(1′-k)
(1′-l)
Examples of other copolymerizable compound to be copolymerized (hereinafter referred to as "copolymerizable monomer") include compounds represented by the following formulae (I) to (X) (in the formulae, $R^9$, $R^{10}$, $R^{11}$, $R^{12}$, $R^{14}$, $R^{15}$, $R^{16}$, $R^{17}$, and $R^{18}$ each independently represents a hydrogen atom or a methyl group; and $R^{13}$ represents a hydrogen atom or $COOR^{19}$ ($R^{19}$ represents an alkyl group, for example, a methyl group, an ethyl group, an n-propyl group, etc.; or a cycloalkyl group, for example, a cyclohexyl group, a cyclopentyl group, a 2-adamantyl group, etc.)). But, it should not be construed that the present invention is limited thereto. The copolymerizable monomer can be used singly or can be used in admixture of two or more kinds thereof as the need arises.

(I)
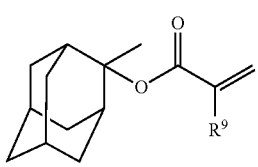

(II)
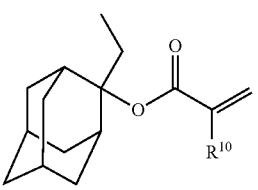

(III)
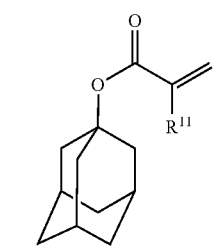

(IV)
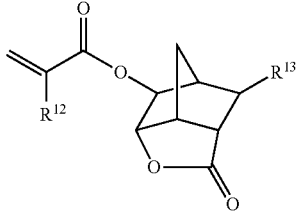

(V)
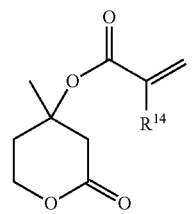

(VI)
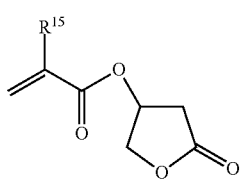

-continued (VII)
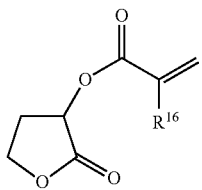

(VIII)
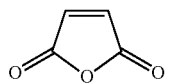

(VIIII)
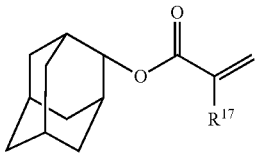

(X)
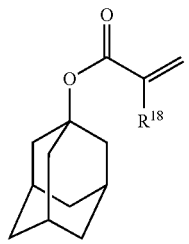

Specific examples of the polymer compound (4) of the present invention include the following polymer compounds, but it should not be construed that the present invention is limited thereto. ($R^9$, $R^{10}$, $R^{11}$, $R^{12}$, $R^{14}$, $R^{15}$, $R^{16}$, $R^{17}$ and $R^{18}$ are the same as defined above; and l, m and n each represents a molar ratio of the constitutional unit.)

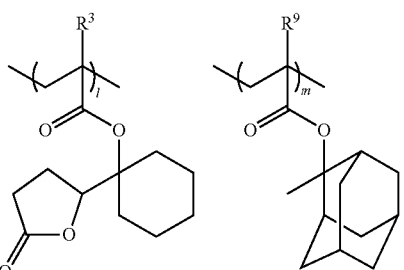

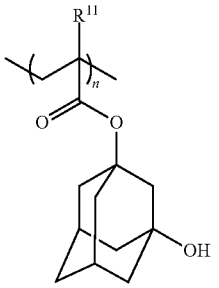

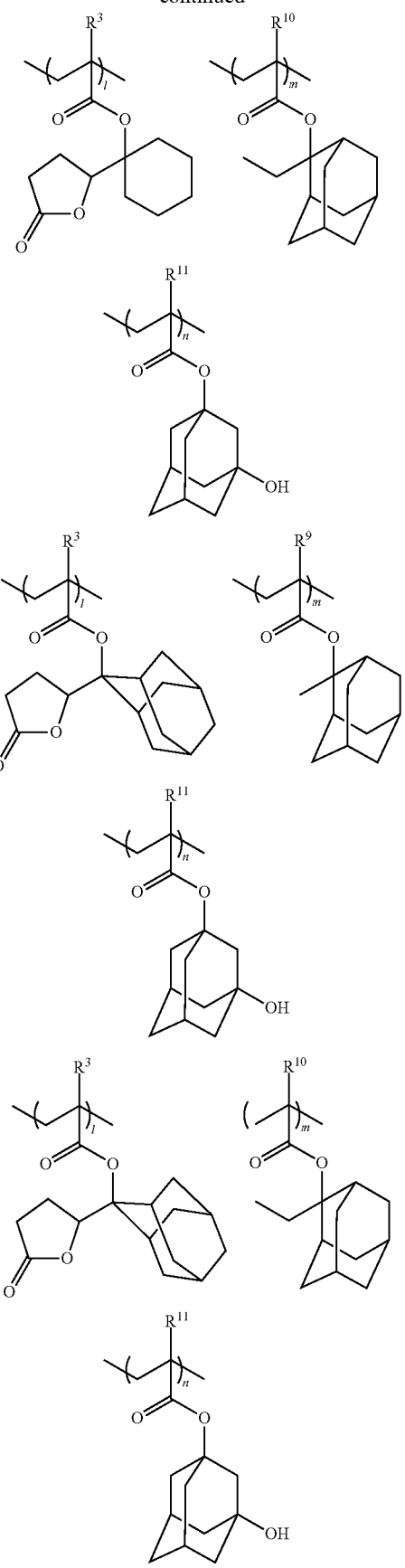
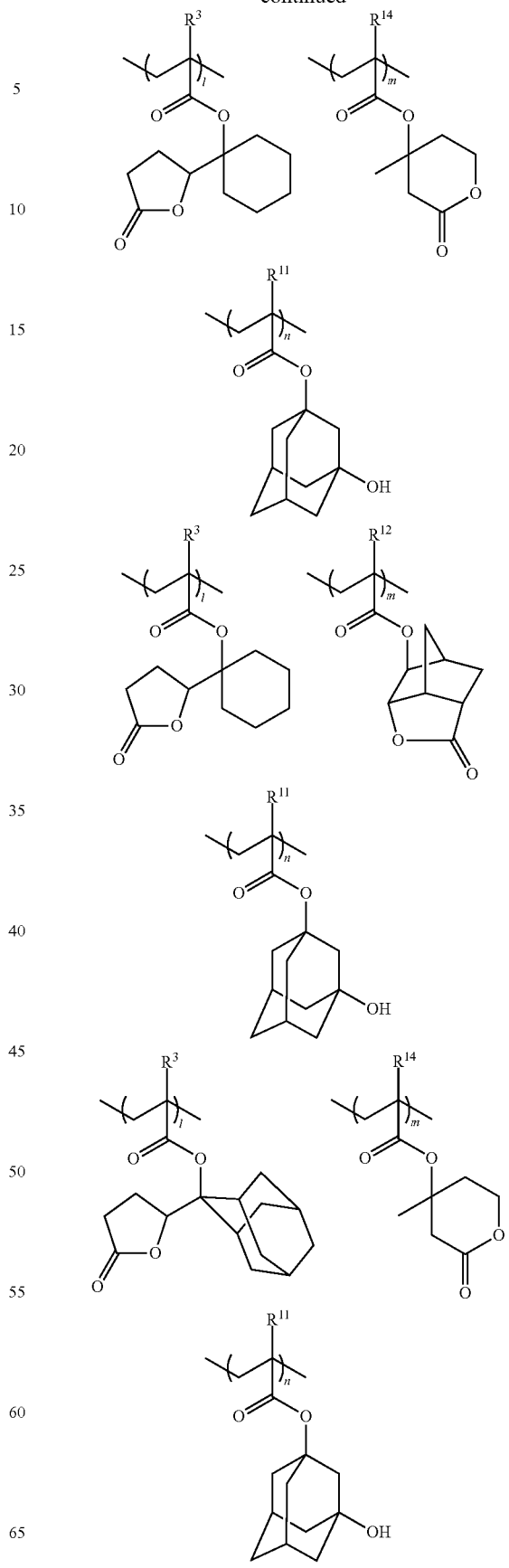

-continued
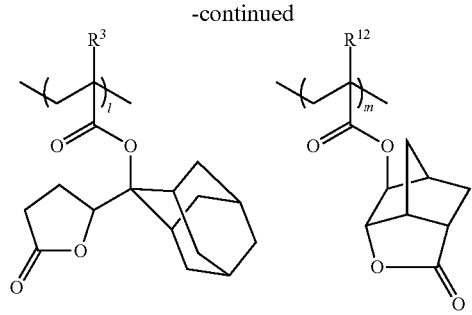
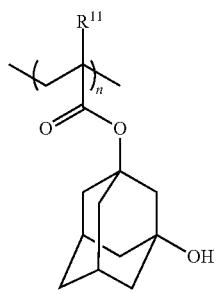
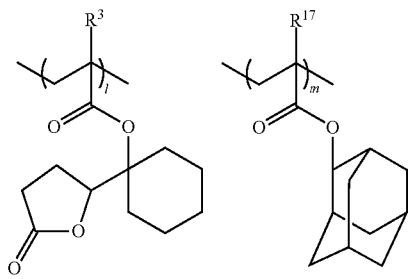
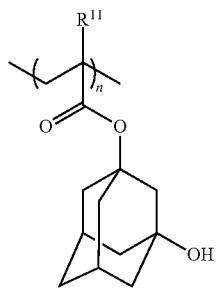
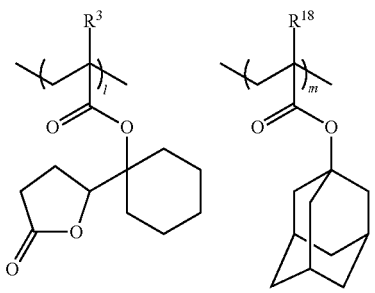
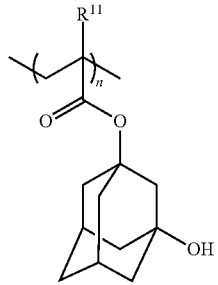
-continued
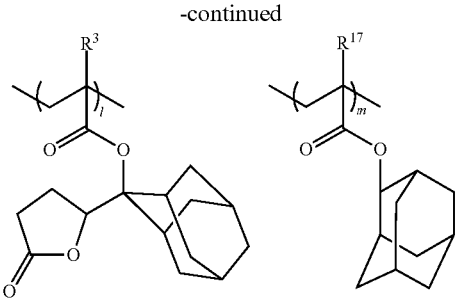
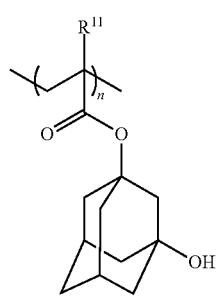
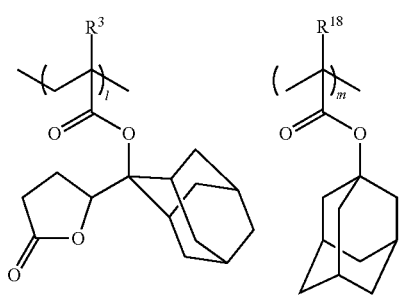
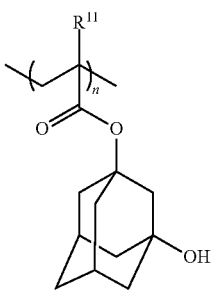
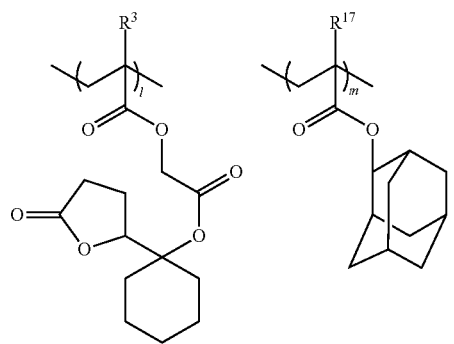

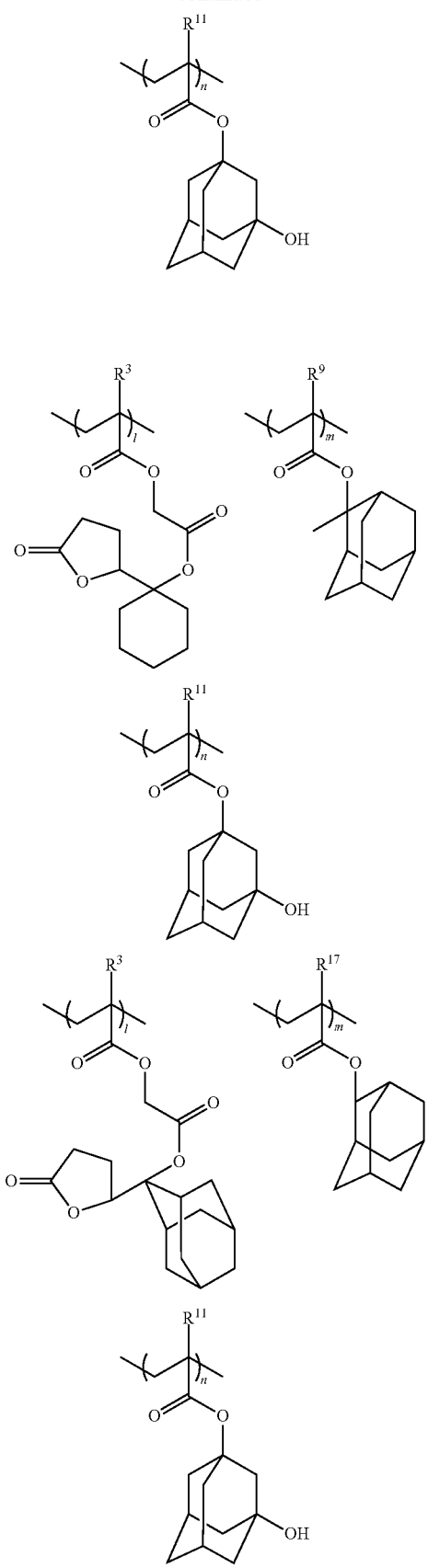

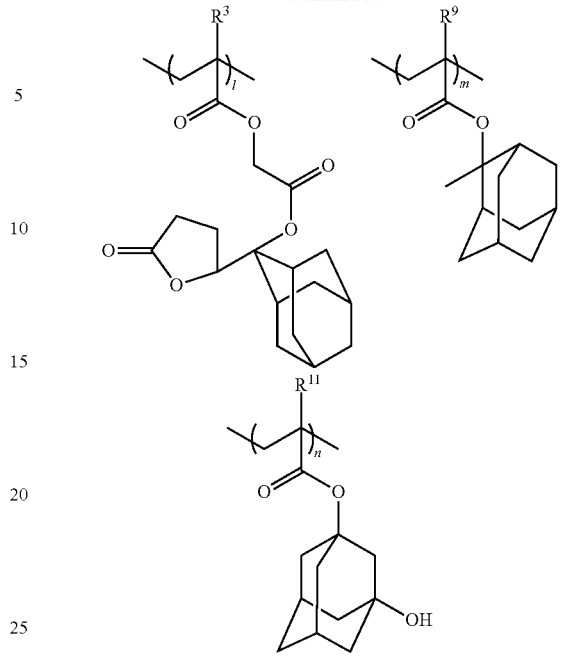

Though the polymer compound (4) of the present invention is not particularly limited with respect to its weight average molecular weight (Mw), a polymer having an Mw according to the following measurement method in the range of from 500 to 50,000, and preferably in the range of from 1,000 to 30,000 is useful as a raw material of a polymer composition for photoresist. In the measurement, such Mw can be determined by a gel permeation chromatography method (GPC method) using a column prepared by connecting two columns of TSK-gel SUPER HZM-H (a trade name, manufactured by Tosoh Corporation; diameter: 4.6 mm, length: 150 mm) and one column of TSK-gel SUPER HZ2000 (a trade name, manufactured by Tosoh Corporation; diameter: 4.6 mm, length: 150 mm) in series; using a differential refractometer (RI) as a detector and tetrahydrofuran as an eluting solution; measuring under a condition at a column temperature of 40° C., a temperature of RI of 40° C. and a flow rate of the eluting solution of 0.35 mL/min; and calculating according to a calibration curve prepared using standard polystyrene. Also, by dividing a weight average molecular weight (Mw) by a number average molecular weight (Mn), dispersity (Mw/Mn) is determined.

The dispersity of the polymer compound (4) of the present invention is preferably in the range of from 1.0 to 2.5, and more preferably in the range of from 1.0 to 2.0.

The polymer compound (4) of the present invention is obtained by feeding the tertiary alcohol derivative (1) and a radical polymerization initiator and optionally, one or more kinds of copolymerizable monomers, a solvent and a chain transfer agent into a reactor and subjecting the mixture to a radical polymerization reaction. Such a polymerization reaction is hereunder described.

In the manufacture of the polymer compound (4) of the present invention, the tertiary alcohol derivative (1) as a monomer and the copolymerizable monomer are polymerized in a corresponding molar ratio of the constitutional units in the desired polymer compound (4). That is, similar to a manner which is carried out in a general radical polymerization reaction, taking into consideration a polymerization rate ratio of each monomer and a corresponding molar ratio of the constitutional units in the desired polymer compound (4), by properly regulating a molar ratio of the tertiary alcohol derivative (1) and the copolymerizable monomer to be provided for the radical polymerization reaction, the polymer compound (4) having a desired molar ratio of the constitutional units can be obtained.

Examples of the radical polymerization initiator to be used for the manufacture of the polymer compound (4) of the present invention include hydroperoxide compounds, for example, t-butylhydroperoxide, etc.; dialkylperoxide compounds, for example, di-t-butylperoxide, etc.; diacyl peroxide compounds, for example, benzoyl peroxide, etc.; and azo compounds, for example, 2,2'-azobisisobutyronitrile, dimethyl 2,2'-azobisisobutyrate, etc. Above all, it is preferable to use an azo compound, for example, 2,2'-azobisisobutyronitrile, dimethyl 2,2'-azobisisobutyrate, etc. The use amount of the radical polymerization initiator is preferably in the range of from 0.5% by mole to 20% by mole, and more preferably in the range of from 1 to 15% by mole relative to the total molar number of the polymerizable compounds, namely the total molar number of the tertiary alcohol derivative (1) and other copolymerizable monomer. Similar to a general radical polymerization reaction, the molecular weight of the polymer compound (4) can be regulated by the use amount of the radical polymerization initiator.

In the manufacture of the polymer compound (4) of the present invention, a chain transfer agent may be used as the need arises. Examples of the chain transfer agent include thiol compounds, for example, dodecanethiol, mercaptoethanol, mercaptopropanol, mercaptoacetic acid, mercaptopropionic acid, etc. These may be used singly or may be used in admixture of two or more kinds thereof. In case of using a chain transfer agent, the use amount thereof is preferably in the range of from 0.5% by mole to 20% by mole, and more preferably in the range of from 1 to 15% by mole relative to the total molar number of the polymerizable compounds, namely the total molar number of the tertiary alcohol derivative (1) and other copolymerizable monomer.

It is preferable that the manufacture of the polymer compound (4) of the present invention is carried out in a solvent. The solvent is not particularly limited so far as it does not hinder the polymerization reaction, and examples thereof include glycol ethers, for example, propylene glycol monoethyl ether, propylene glycol monomethyl ether acetate, ethylene glycol monomethyl ether, ethylene glycol monomethyl ether acetate, ethylene glycol monobutyl ether, ethylene glycol monobutyl ether acetate, etc.; esters, for example, ethyl lactate, methyl 3-methoxypropionate, methyl acetate, ethyl acetate, propyl acetate, etc.; ketones, for example, acetone, methyl ethyl ketone, methyl isopropyl ketone, methyl isobutyl ketone, methyl amyl ketone, cyclohexanone, etc.; and ethers, for example, diethyl ether, diisopropyl ether, dibutyl ether, tetrahydrofuran, dioxane, etc. These may be used singly or may be used in admixture of two or more kinds thereof. From the viewpoints of economy and easiness of post-treatment, in general, the use amount of the solvent is preferably in the range of from 0.5 times by mass to 20 times by mass, and preferably in the range of from 1 time by mass to 10 times by mass relative to the total mass of the polymerizable compounds, namely the total molar number of the tertiary alcohol derivative (1) and other copolymerizable monomer.

In the manufacture of the polymer compound (4) of the present invention, the polymerization method is not particularly limited, and a known method which is employed in manufacturing an acrylic polymer, including a solution polymerization method, an emulsion polymerization method, a suspension polymerization method and a bulk polymerization method, can be employed. Above all, it is preferable to employ a solution polymerization method.

From the viewpoint of stability of the tertiary alcohol derivative (1) and the polymer compound (4), the polymerization temperature in the manufacture of the polymer compound (4) of the present invention is in the range of from 40° C. to 150° C., and preferably in the range of from 60° C. to 120° C.

The manufacturing time of the polymer compound (4) of the present invention varies depending upon the kind and amount of the tertiary alcohol derivative (1); the kind and amount of the copolymerizable monomer; the kind and amount of the radical polymerization initiator; the kind and amount of the solvent; the temperature of the polymerization reaction; and the like, and it is generally in the range of from 30 minutes to 48 hours, and preferably in the range of from 1 hour to 24 hours.

It is possible to isolate the polymer compound (4) to be contained in the thus obtained reaction mixed solution by a usual operation, for example, gel permeation chromatography, reprecipitation, etc. Also, it is possible to regulate the molecular weight and dispersity by a usual operation, for example, gel permeation chromatography, reprecipitation, etc. Furthermore, if desired, it is possible to reduce the content of a metal in the polymer compound (4) by dissolving the isolated polymer compound (4) in an appropriate solvent and subjecting the solution to an operation, for example, a treatment with a chelating agent, a treatment by a metal removal filter, etc.

Examples of the solvent to be used for the foregoing reprecipitation include aliphatic hydrocarbons, for example, pentane, hexane, etc.; alicyclic hydrocarbons, for example, cyclohexane, etc.; aromatic hydrocarbons, for example, benzene, xylene, etc.; halogenated hydrocarbons, for example, methylene chloride, chloroform, chlorobenzene, dichlorobenzene, etc.; nitrated hydrocarbons, for example, nitromethane, etc.; nitriles, for example, acetonitrile, benzonitrile, etc.; ethers, for example, diethyl ether, diisopropyl ether, tetrahydrofuran, 1,4-dioxane, etc.; ketones, for example, acetone, methyl ethyl ketone, etc.; carboxylic acids, for example, acetic acid, etc.; acetic acid esters, for example, ethyl acetate, butyl acetate, etc.; carbonates, for example, dimethyl carbonate, diethyl carbonate, ethylene carbonate, etc.; and alcohols, for example, methanol, ethanol, propanol, isopropanol, butanol, etc. These solvents may be used singly or may be used in admixture of two or more kinds thereof.

The photoresist composition of the present invention is composed of the foregoing polymer compound (4) of the present invention and a solvent and a photo acid generator and optionally, a basic substance and additives as described later.

Examples of the solvent to be used for the photoresist composition of the present invention include glycol ethers, for example, propylene glycol monoethyl ether, propylene glycol monomethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, etc.; esters, for example, ethyl lactate, methyl 3-methoxypropionate, methyl acetate, ethyl acetate, propyl acetate, etc.; ketones, for example, acetone, methyl ethyl ketone, methyl isopropyl ketone, methyl isobutyl ketone, methyl amyl ketone, cyclopentanone, cyclohexanone, etc.; and ethers, for example, diethyl ether, diisopropyl ether, dibutyl ether, tetrahydrofuran, 1,4-dioxane, etc. The solvent may be used singly or may be used in admixture of two or more kinds thereof. The use amount of the solvent is usually in the range of from 1 time by mass to 50 times by mass, and preferably in the range of from 2 times by mass to 25 times by mass relative to the polymer compound (4).

As the photo acid generator to be used for the photoresist composition of the present invention, a customary known compound capable of efficiently forming an acid upon exposure can be used. Examples of the photo acid generator include sulfonium salts, for example, triphenylsulfonium hexafluoroantimonate, triphenylsulfonium hexafluorophosphate, triphenylsulfonium trifluoromethyl methanesulfonate, triphenylsulfonium nonafluorobutanesulfonate, etc.; iodonium salts, for example, diphenyliodohexafluorosulfate, etc.; disulfones, for example, diphenyldisulfone, ditolylsulfone, etc.; triazine derivatives, for example, 1-methyl-3,5-bis-trichloromethyltriazine, 1,3,5-tristrichloromethyltriazine, etc.; diazomethane derivatives, for example, bis(cyclohexylsulfonyl)diazomethane, bis(phenylsulfonyl)diazomethane, etc.; sulfonic acid esters, for example, (2'-nitrophenyl)methyl-p-toluenesulfonate, (2',6'-dinitrophenyl)methyl-p-toluenesulfonate, 1-phenyl-1-(4-methylphenyl)sulfonyloxy-1-benzoylmethane, etc.; diazonaphthoquinone; and benzoin tosylate. These photo acid generators can be used singly or can be used in admixture of two or more kinds thereof. The use amount of the photo acid generator can be chosen depending upon the strength of an acid which is formed upon irradiation with radiations or the amount of the constitutional unit to be derived from the tertiary alcohol derivative (1) in the polymer compound (4) and is in the range of from 0.1% by mass to 30% by mass, and preferably from 0.5% by mass to 10% by mass relative to the polymer compound (4).

The photoresist composition of the present invention may further contain a basic substance as the need arises. Examples of the basic substance include amides, for example, formamide, N-methylformamide, N,N-dimethylformamide, acetamide, N-methylacetamide, N,N-dimethylacetamide, N-(1-adamantyl)acetamide, benzamide, N-acetylethanolamine, 1-acetyl-3-methylpiperidine, pyrrolidone, N-methylpyrrolidone, ε-caprolactam, δ-valerolactam, 2-pyrrolidinone, acrylamide, methacrylamide, t-butyl acrylamide, methylenebisacrylamide, methylenebismethacrylamide, N-methylolacrylamide, N-methoxyacrylamide, diacetone acrylamide, etc.; and amines, for example, pyridine, 2-methylpyridine, 4-methylpyridine, nicotine, quinoline, acridine, imidazole, 4-methylimidazole, benzimidazole, pyrazine, pyrazole, pyrrolidine, piperidine, tetrazole, morpholine, 4-methylmorpholine, piperazine, diazabicyclo[2,2,2]octane, tributylamine, tripentylamine, trihexylamine, triheptylamine, trioctylamine, triethanolamine, etc. These basic substances may be used singly or may be used in admixture of two or more kinds thereof. In case of using a basic substance, though the use amount thereof varies depending upon the kind of the basic substance, the basic substance is usually used in an amount in the range of from 0.01 times by mole to 10 times by mole, and preferably in the range of from 0.05 times by mole to 1 time by mole relative to the photo acid generator.

Furthermore, the photoresist composition of the present invention can also be blended with various additives, for example, a surfactant, a sensitizer, an anti-halation agent, a storage stabilizer, an anti-foaming agent, etc. as the need arises.

A pattern can be formed by coating the photoresist composition of the present invention on a substrate, prebaking at a temperature of from about 70° C. to 160° C., irradiating with radiations, especially an ArF excimer laser, then post-exposure baking at a temperature of from 70° C. to 160° C. for 30 seconds or more and subsequently developing with water or an alkaline developing solution.

For the exposure of the photoresist composition of the present invention, radiations having a wavelength of every kind, for example, ultraviolet rays, X-rays, etc. can be utilized. In the use for semiconductor resist, excimer lasers, for example, g-rays, i-rays, XeCl, KrF, KrCl, ArF, ArCl, $F_2$, etc. are usually used. The exposure energy is preferably in the range of from 0.1 to 1,000 $mJ/cm^2$, and more preferably in the range of from 1 to 500 $mJ/cm^2$.

EXAMPLES

The present invention is specifically described below with reference to the following Examples, but it should not be construed that the present invention is limited to these Examples. A weight average molecular weight (Mw) and dispersity (Mw/Mn) of a polymer compound were measured by a GPC analysis [column: one prepared by connecting two columns of TSK-gel SUPER HZM-H (a trade name, manufactured by Tosoh Corporation; diameter: 4.6 mm, length: 150 mm) and one column TSK-gel SUPER HZ2000 (a trade name, manufactured by Tosoh Corporation; diameter: 4.6 mm, length: 150 mm) in series; detector: differential refractometer (RI); column temperature: 40° C.; RI temperature: 40° C.; eluting solution: tetrahydrofuran; flow rate of the eluting solution: 0.35 mL/min; calibration curve: standard polystyrene].

Synthesis Example 1

Synthesis of methyl 4-cyclohexylidenebutanoate

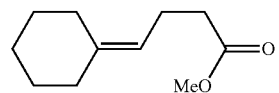 [SMILES: COC(=O)CCC=C1CCCCC1]

A distillation column-provided four-necked flask having a volume of one liter, which was equipped with a dropping funnel, a thermometer, a stirring device and a reflux ratio regulator, was charged with 250 g (1.922 moles) of 1-vinyl-1-cyclohexanol, 415.6 g (3.843 moles) of trimethyl orthoacetate and 1.4 g (0.019 moles) of propionic acid, and the internal temperature was raised to 115° C. Heating was continued for 12 hours while removing a fraction of not higher than 65° C. from a column top of the distillation column. After confirming the disappearance of 1-vinyl-1-cyclohexanol by a gas chromatographic analysis of the reaction solution, the reaction solution was distilled in vacuo. Fractions of from 120 to 130° C./1.2 kPa were collected to obtain 301.2 g (1.653 moles) of methyl 4-cyclohexylidenebutanoate. The yield was 86.0%.

$^1$H-NMR (300 MHz, $CDCl_3$, ppm, TMS) δ:
5.03 (1H, br), 3.66 (3H, s), 2.32 (4H, m), 2.13 (2H, br), 2.05 (2H, br), 1.52 (6H, m)

Example 1

Synthesis of 4-(1'-hydroxycyclohexan-1'-yl)butanolide

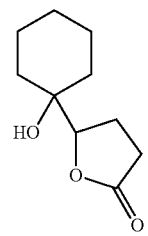

A four-necked flask having a volume of one liter, which was equipped with a dropping funnel, a thermometer and a reflux condenser, was charged with 256.4 g (1.407 moles) of methyl 4-cyclohexylidenebutanoate as obtained in the method of Synthesis Example 1, 260 g of water and 97.1 g (2.110 moles) of formic acid, and the internal temperature was raised to 50° C. To this mixed solution, 239.2 g (2.111 moles) of 30% by mass hydrogen peroxide water was added dropwise over 3 hours. After completion of the dropwise addition, the mixture was stirred at 50° C. for 6 hours and then cooled to 25° C. 106.3 g (0.844 moles) of sodium sulfite was added to the reaction mixture while maintaining the internal temperature at not higher than 35° C. This reaction mixed solution was separated into an organic layer and an aqueous layer. 389.2 g of the organic layer was distilled in vacuo. Fractions of 160° C./67 Pa were collected to obtain 228.1 g (1.238 moles) of 4-(1'-hydroxycyclohexan-1'-yl)butanolide. The yield was 88.0%.

$^1$H-NMR (300 MHz, CDCl$_3$, ppm, TMS) δ:

4.34 (1H, t, J=7.5 Hz), 2.63 to 2.50 (2H, m), 2.35 to 2.2 (2H, m), 2.2 to 2.05 (1H, m), 1.75 (1H, d, J=12.8 Hz), 1.71 to 1.42 (7H, m), 1.28 (2H, m)

Boiling point: 160° C./67 Pa

Example 2

Synthesis of 4-(1'-methacryloyloxycyclohexan-1'-yl)butanolide

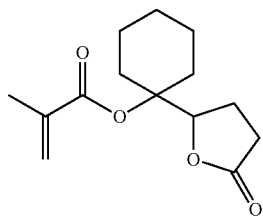 [SMILES: C=C(C)C(=O)OC1(C2CCC(=O)O2)CCCCC1]

A four-necked flask having an inner volume of 300 mL, which was equipped with a dropping funnel, a thermometer and a nitrogen introducing pipe, was charged with 30 g (162.8 mmoles) of 4-(1'-hydroxycyclohexan-1'-yl)butanolide as obtained in the method of Example 1, 100 mL of methylene chloride, 1.0 g (8.1 mmoles) of dimethylaminopyridine and 28.9 g (276.8 mmoles) of methacryloyl chloride. To this mixed solution, 29.7 g (293.0 mmoles) of triethylamine was added dropwise at room temperature over 30 minutes. After completion of the dropwise addition, the mixture was stirred at room temperature for 20 hours. To the reaction mixture, 6.3 g (136.8 mmoles) of ethanol was added dropwise, 100 mL of water was subsequently added dropwise, and the mixture was stirred for 15 minutes. This reaction mixed solution was separated into an organic layer and an aqueous layer. The organic layer was washed with 50 mL of water and then concentrated in vacuo. To 37 g of the concentrate, 70 mL of methyl isopropyl ketone was added, and the mixture was cooled to −76° C. while stirring. The resulting mixture was stirred at −76° C. for 3 hours, and a deposited crystal of 4-(1'-methacryloyloxycyclohexan-1'-yl)butanolide was then filtered. The obtained crystal was 16.4 g (65.1 mmoles), and the yield was 40.0%. A gas chromatographic analysis revealed that the filtrate contained 14.4 g (57.2 mmoles) of 4-(1'-methacryloyloxycyclohexan-1'-yl)butanolide. A total yield was 75.1%.

$^1$H-NMR (300 MHz, CDCl$_3$, ppm, TMS) δ:

6.10 (1H, s), 5.58 (1H, s), 5.34 (1H, t, J=7.8 Hz), 2.57 to 2.50 (2H, m), 2.44 (1H, d, J=11.1 Hz), 2.19 to 2.08 (3H, m), 1.94 (3H, s), 1.71 to 1.44 (7H, m), 1.28 (1H, m)

Melting point: 57.1 to 58.4° C.

Synthesis Example 2

Synthesis of methyl 4-adamantylidenebutanoate

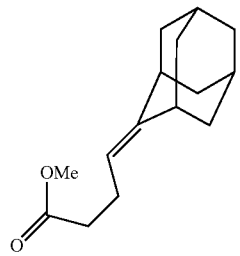 [SMILES: COC(=O)CCC=C1C2CC3CC(C2)CC1C3]

A distillation column-provided four-necked flask having a volume of 100 mL, which was equipped with a dropping funnel, a thermometer, a stirring device and a reflux ratio regulator, was charged with 25.0 g (140.2 mmoles) of 2-vinyl-2-adamantanol, 30.3 g (280.5 mmoles) of trimethyl orthoacetate and 0.2 g (2.8 mmoles) of propionic acid, and the internal temperature was raised to 115° C. Heating was continued for 16 hours while removing a fraction of not higher than 65° C. from a column top of the distillation column. At that time, 0.2 g (2.8 mmoles) of propionic acid was added 16 times every one hour. The reaction mixture was concentrated at 110° C. under atmospheric pressure to obtain 26.9 g (115.0 mmoles) of methyl 4-adamantylidenebutanoate. The yield was 82.0%.

$^1$H-NMR (300 MHz, CDCl$_3$, ppm, TMS) δ:

5.00 (1H, m), 3.67 (3H, s), 2.81 (1H, s), 2.31 (5H, br), 1.93 to 1.65 (12H, m)

Example 3

Synthesis of 4-(2'-hydroxyadamantan-2'-yl)butanolide

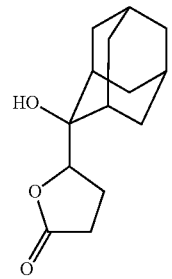 [SMILES: O=C1CCC(C2(O)C3CC4CC(C3)CC2C4)O1]

A four-necked flask having a volume of 100 mL, which was equipped with a dropping funnel, a thermometer and a reflux condenser, was charged with 25.0 g (106.7 mmoles) of methyl 4-adamantylidenebutanoate as obtained in the method of Synthesis Example 2, 63 g of water and 7.4 g (160.1 mmoles) of formic acid, and the internal temperature was raised to 50° C. To this mixed solution, 18.2 g (160.1 mmoles) of 30% by mass hydrogen peroxide water was added dropwise over 3 hours. After completion of the dropwise addition, the mixture was stirred at 50° C. for 6 hours and then cooled to 25° C. 8.1 g (64.1 mmoles) of sodium sulfite was added to the reaction mixture while maintaining the internal temperature at not higher than 35° C. This reaction mixed solution was filtered, and the obtained crystal was washed with 20 g of water and then dried in vacuo to obtain 17.0 g (71.8 mmoles) of 4-(2'-hydroxyadamantan-2'-yl)butanolide. The yield was 67.3%.

¹H-NMR (300 MHz, CDCl₃, ppm, TMS) δ:

5.10 (1H, t, J=8.1 Hz), 2.62 to 2.58 (2H, m), 2.36 to 2.01 (6H, m), 1.96 to 1.72 (9H, m), 1.58 (2H, t, J=12.6 Hz)

Melting point: 135.7 to 137.4° C.

Example 4

Synthesis of 4-(2'-methacryloyloxyadamantan-2'-yl)butanolide

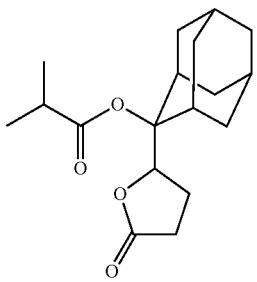 [SMILES: CC(C)C(=O)OC1(C2CCC(=O)O2)C2CC3CC(C2)CC1C3]

A four-necked flask having a volume of 300 mL, which was equipped with a dropping funnel, a thermometer and a nitrogen introducing pipe, was charged with 10.0 g (42.3 mmoles) of 4-(2'-hydroxyadamantan-2'-yl)butanolide as obtained in the method of Example 3, 50 mL of methylene chloride, 0.26 g (2.1 mmoles) of dimethylaminopyridine and 6.6 g (63.5 mmoles) of methacryloyl chloride. To this mixed solution, 7.8 g (69.9 mmoles) of diazabicyclo[2,2,2]octane was added dropwise at room temperature over 30 minutes. After completion of the dropwise addition, the mixture was stirred at room temperature for 20 hours. To the reaction mixed solution, 2.0 g (42.4 mmoles) of ethanol was added dropwise, 20 mL of water was subsequently added dropwise, and the mixture was stirred for 15 minutes. This reaction mixed solution was separated into an organic layer and an aqueous layer. The organic layer was washed with 20 mL of water and then concentrated in vacuo. The concentrate was purified by silica gel column chromatography to obtain 6.7 g (21.9 mmoles) of 4-(2'-methacryloyloxyadamantan-2'-yl)butanolide. The yield was 51.8%.

¹H-NMR (300 MHz, CDCl₃, ppm, TMS) δ:

6.10 (1H, s), 5.57 (1H, s), 5.26 (1H, dd, J=5.4 Hz, 8.4 Hz), 2.76 (1H, s), 2.62 (1H, s), 2.53 to 2.38 (3H, m), 2.26 to 2.23 (1H, m), 2.07 to 2.02 (1H, m), 1.97 to 1.93 (3H, m), 1.93 (3H, s), 1.86 to 1.81 (4H, m), 1.77 (2H, brs), 1.71 to 1.64 (2H, m)

Synthesis Example 3

Synthesis of 4-(1'-chloroacetoxycyclohexan-1'-yl)butanolide

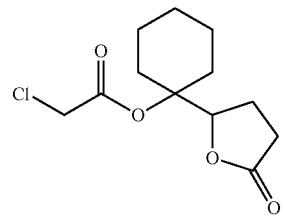 [SMILES: O=C1CCC(C2(OC(=O)CCl)CCCCC2)O1]

A four-necked flask having a volume of 300 mL, which was equipped with a dropping funnel, a thermometer and a nitrogen introducing pipe, was charged with 30 g (162.8 mmoles) of 4-(1'-hydroxycyclohexan-1'-yl)butanolide as obtained in the method of Example 1, 100 mL of methylene chloride, 1.0 g (8.1 mmoles) of dimethylaminopyridine and 31.3 g (276.8 mmoles) of 2-chloroacetyl chloride. To this mixed solution, 29.7 g (293.0 mmoles) of triethylamine was added dropwise over 30 minutes. After completion of the dropwise addition, the mixture was stirred at room temperature for 20 hours. To the reaction mixed solution, 6.3 g (136.8 mmoles) of ethanol was added dropwise, 100 mL of water was subsequently added dropwise, and the mixture was stirred for 15 minutes. This reaction mixed solution was separated into an organic layer and an aqueous layer; and the organic layer was washed with 50 mL of water and then concentrated in vacuo to obtain 35.2 g (135.1 mmoles) of 4-(1'-chloroacetoxycyclohexan-1'-yl)butanolide. The yield was 83.0%.

¹H-NMR (300 MHz, CDCl₃, ppm, TMS) δ:

4.87 (1H, t, J=7.7 Hz), 4.35 (2H, s), 2.36 to 2.30 (2H, m), 2.06 (2H, d, J=11.2 Hz), 1.67 to 1.65 (4H, m), 1.50 to 1.42 (6H, m)

Example 5

Synthesis of 4-(1'-methacryloyloxyacetoxycyclohexan-1'-yl)butanolide

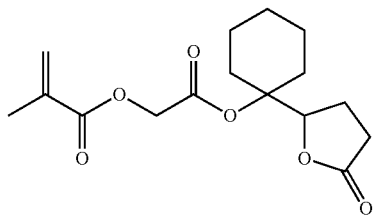 [SMILES: C=C(C)C(=O)OCC(=O)OC1(C2CCC(=O)O2)CCCCC1]

A four-necked flask having a volume of 500 mL, which was equipped with a dropping funnel, a thermometer and a nitrogen introducing pipe, was charged with 35.2 g (135.1 mmoles) of 4-(1'-chloroacetoxycyclohexan-1'-yl)butanolide as obtained in the method of Synthesis Example 3, 13.1 g (94.6 mmoles) of potassium carbonate, 0.5 g (1.4 mmoles) of tetrabutylammonium iodide and 150 mL of toluene. To this mixed solution, 15.1 g (175.6 mmoles) of methacrylic acid was added dropwise at room temperature over 30 minutes.

After completion of the dropwise addition, the mixture was heated to 50° C. and stirred for 10 hours. After cooling the reaction solution to room temperature, 150 mL of water and 100 mL of ethyl acetate were added. This mixed solution was separated into an organic layer and an aqueous layer; and the organic layer was concentrated in vacuo and then purified by silica gel column chromatography to obtain 30.6 g (98.6 mmoles) of 4-(1'-methacryloyloxyacetoxycyclohexan-1'-yl)butanolide. The yield was 72.9%.

$^1$H-NMR (300 MHz, CDCl$_3$, ppm, TMS) δ:
6.15 (1H, s), 5.59 (1H, s), 5.13 (2H, s), 4.88 (1H, t, J=7.5 Hz), 2.36 to 2.30 (2H, m), 2.06 (2H, d, J=11.5 Hz), 1.94 (3H, s), 1.67 to 1.65 (4H, m), 1.50 to 1.42 (6H, m)<

Synthesis Example 4

Synthesis of 3-(1'-methacryloyloxycyclohexan-1'-yl)butanolide

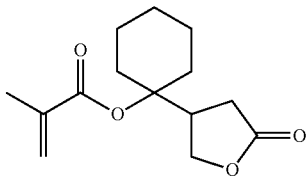 [SMILES: C=C(C)C(=O)OC1(C2COC(=O)C2)CCCCC1]

A four-necked flask having a volume of 100 mL, which was equipped with a dropping funnel and a thermometer, was charged with 10.0 g (118.9 mmoles) of 2(5H)-furanone, 11.9 g (118.9 mmoles) of cyclohexanol and 5.2 g (35.7 mmoles) of di-t-butyl peroxide, and the mixture was heated to 130° C. After stirring for 20 hours, the reaction mixture was cooled to 25° C. After adding 18.0 g (178.4 mmoles) of triethylamine and 30 mL of methylene chloride to the reaction mixture, 14.9 g (142.7 mmoles) of methacryloyl chloride was added dropwise at 25° C. After completion of the dropwise addition, the mixture was stirred at 25° C. for 13 hours, and 30 mL of water was then added dropwise. The reaction mixture was separated into an organic layer and an aqueous layer, and the aqueous layer was extracted twice with 30 mL of methylene chloride. The organic layer and the extract were mixed and concentrated in vacuo. The concentrate was purified by silica gel column chromatography to obtain 1.7 g (6.9 mmoles) of 3-(1'-methacryloyloxycyclohexan-1'-yl)butanolide. The yield was 5.8%.

$^1$H-NMR (300 MHz, CDCl$_3$, ppm, TMS) δ:
6.16 (1H, s), 5.56 (1H, s), 4.28 (2H, t, J=7.6 Hz), 2.65 (1H, m), 2.30 (2H, t, J=7.6 Hz), 1.92 (3H, s), 1.65 to 1.60 (4H, m), 1.51 to 1.43 (6H, m)

Synthesis Example 5

Synthesis of 2-(1'-methacryloyloxycyclohexan-1'-yl)butanolide

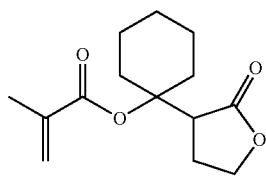 [SMILES: C=C(C)C(=O)OC1(C2CCOC2=O)CCCCC1]

A four-necked flask having a volume of 500 mL, which was equipped with a dropping funnel, a thermometer and a nitrogen introducing pipe, was charged with 100 mL of tetrahydrofuran and 9.3 g (232.3 mmoles) of 60% by mass sodium hydride. This mixed solution was cooled to −10° C., and a solution of 20.0 g (232.3 mmoles) of γ-butyrolactone in tetrahydrofuran (20 mL) was added dropwise over one hour. After completion of the dropwise addition, the internal temperature was raised to 0° C., and the mixture was stirred for 3 hours. Next, a solution of 22.8 g (232.3 mmoles) of cyclohexanone in tetrahydrofuran (20 mL) was added dropwise at an internal temperature of 0° C. over one hour. After completion of the dropwise addition, the mixture was stirred at the same temperature for 5 hours. Subsequently, 26.7 g (255.5 mmoles) of methacryloyl chloride was added dropwise at 0° C. over one hour. After completion of the dropwise addition, the temperature was raised to 30° C., and the mixture was stirred for 7 hours. After adding 50 mL of water and 200 mL of ethyl acetate to the reaction mixture, the mixture was separated into an organic layer and an aqueous layer. The organic layer was concentrated in vacuo, and the concentrate was purified by silica gel column chromatography to obtain 8.8 g (34.8 mmoles) of 2-(1'-methacryloyloxycyclohexan-1'-yl)butanolide.

$^1$H-NMR (300 MHz, CDCl$_3$, ppm, TMS) δ:
6.13 (1H, s), 5.58 (1H, s), 4.33 (2H, br), 2.90 (1H, t, J=7.8 Hz), 2.10 to 2.02 (2H, m), 1.93 (3H, s), 1.67 to 1.65 (4H, m), 1.50 to 1.42 (6H, m)

Synthesis Example 6

Synthesis of methyl 5-methyl-4-hexenate

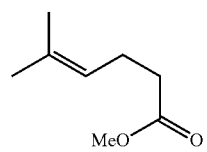

A distillation column-provided four-necked flask having a volume of one liter, which was equipped with a dropping funnel, a thermometer, a stirring device and a reflux ratio regulator, was charged with 50.0 g (580.5 mmoles) of 2-vinyl-2-propanol, 139.5 g (1,161.0 mmoles) of trimethyl orthoacetate and 1.3 g (17.4 mmoles) of propionic acid, and the internal temperature was raised to 115° C. Heating was continued for 12 hours while removing a fraction of not higher than 65° C. from a column top of the distillation column. After confirming the disappearance of 2-vinyl-2-propanol by a gas chromatographic analysis of the reaction solution, the reaction solution was distilled in vacuo. Fractions of from 60 to 65° C./1.2 kPa were collected to obtain 62.2 g (437.1 mmoles) of methyl 5-methyl-4-hexenate. The yield was 75.3%.

$^1$H-NMR (300 MHz, CDCl$_3$, ppm, TMS) δ:

5.09 (1H, m), 3.67 (3H, s), 2.30 (4H, br), 1.68 (3H, s), 1.62 (3H, s)

Synthesis Example 7

Synthesis of 4-(2'-hydroxypropan-2'-yl)butanolide

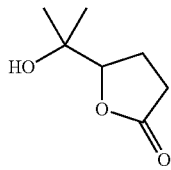

A four-necked flask having a volume of 500 mL, which was equipped with a dropping funnel, a thermometer and a reflux condenser, was charged with 40 g (281.3 mmoles) of methyl 5-methyl-4-hexenate as obtained in the method of Synthesis Example 6, 80 g of water and 20.7 g (450.1 mmoles) of formic acid, and the internal temperature was raised to 50° C. To this mixed solution, 51.0 g (450.1 mmoles) of 30% by mass hydrogen peroxide water was added dropwise over 3 hours. Furthermore, the mixture was stirred at 50° C. for 6 hours and then cooled to 25° C. 25.5 g (202.6 mmoles) of sodium sulfite was added to the reaction mixture while maintaining the internal temperature at not higher than 35° C. This reaction mixed solution was separated into an organic layer and an aqueous layer; the organic layer was concentrated in vacuo; and the obtained concentrated solution was distilled in vacuo. Fractions of 130 to 140° C./400 Pa were collected to obtain 21.3 g (148.0 mmoles) of 4-(2'-hydroxypropan-2'-yl)butanolide. The yield was 52.6%.

$^1$H-NMR (300 MHz, CDCl$_3$, ppm, TMS) δ:
4.32 (1H, t, J=7.5 Hz), 2.60 to 2.53 (2H, m), 2.21 to 2.17 (2H, m), 1.33 (3H, s), 1.19 (3H, s)

Synthesis Example 8

Synthesis of 4-(2'-methacryloyloxypropan-2'-yl) butanolide

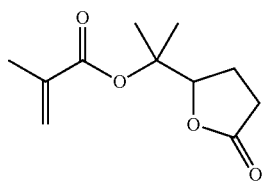

A four-necked flask having a volume of 300 mL, which was equipped with a dropping funnel, a thermometer and a nitrogen introducing pipe, was charged with 10.0 g (69.4 mmoles) of 4-(2'-hydroxypropan-2'-yl)butanolide as obtained in the method of Synthesis Example 7, 50 mL of methylene chloride and 9.4 g (90.2 mmoles) of methacryloyl chloride. To this mixed solution, 11.2 g (111.0 mmoles) of triethylamine was added dropwise over 30 minutes. After completion of the dropwise addition, the mixture was stirred at room temperature for 6 hours. To the reaction mixed solution, 50 mL of water was added dropwise, and the mixture was stirred for 15 minutes and then separated into an organic layer and an aqueous layer. The obtained organic layer was washed with 50 mL of water and then concentrated in vacuo. The concentrate was purified by silica gel column chromatography to obtain 9.4 g (44.3 mmoles) of 4-(2'-methacryloyloxypropan-2'-yl)butanolide. The yield was 63.8%.

$^1$H-NMR (300 MHz, CDCl$_3$, ppm, TMS) δ:
5.98 (1H, s), 5.53 (1H, s), 4.61 (1H, t, J=7.3 Hz), 2.60 (2H, t, J=10.0 Hz), 2.30 to 2.21 (2H, m), 1.90 (3H, s), 1.59 (3H, s), 1.57 (3H, s)

Example 6

Synthesis of Polymer Compound (Polymer Compound 1) Having the Following Structure

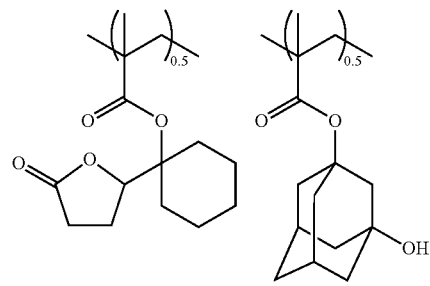

A round bottom flask having a volume of 100 mL, which was equipped with a nitrogen inlet, a stirrer, a reflux condenser and a thermometer, was charged with the whole of 5.9 g (25.0 mmoles) of 1-hydroxy-3-methacryloyloxyadamantane, 6.3 g (25.0 mmoles) of 4-(1'-methacryloyloxycyclohexan-1'-yl)butanolide as obtained in the method of Example 2, 44 mL of methyl ethyl ketone and 0.66 g (4.0 mmoles) of azoisobutyronitrile under a nitrogen atmosphere, and the mixture was heated at 80° C. and polymerized for 4 hours. The obtained reaction solution was added dropwise in 1,000 mL of methanol at room temperature while stirring to obtain a white precipitate. The obtained precipitate was separated by filtration and dried in vacuo for 10 hours to obtain 5.5 g of desired Polymer Compound 1. Mw was 7,400, and Mw/Mn was 1.55.

Example 7

Synthesis of Polymer Compound (Polymer Compound 2) Having the Following Structure

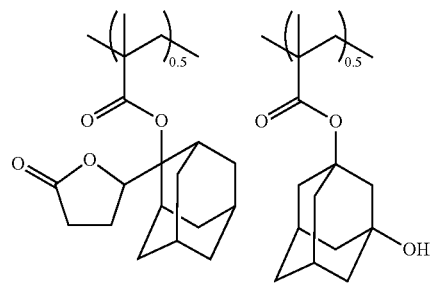

A round bottom flask having a volume of 100 mL, which was equipped with a nitrogen inlet, a stirrer, a reflux condenser and a thermometer, was charged with the whole of 5.9 g (25.0 mmoles) of 1-hydroxy-3-methacryloyloxyadamantane, 7.6 g (25.0 mmoles) of 4-(2'-methacryloyloxyadamantan-2'-yl)butanolide as obtained in the method of Example 4, 44 mL of methyl ethyl ketone and 0.66 g (4.0 mmoles) of azoisobutyronitrile under a nitrogen atmosphere, and the mixture was heated at 80° C. and polymerized for 4 hours. The obtained reaction solution was added dropwise in 1,000 mL of methanol at room temperature while stirring to obtain a white precipitate. The obtained precipitate was separated by filtration and dried in vacuo for 10 hours to obtain 6.5 g of desired Polymer Compound 2. Mw was 7,500, and Mw/Mn was 1.61.

Example 8

Synthesis of Polymer Compound (Polymer Compound 3) Having the Following Structure

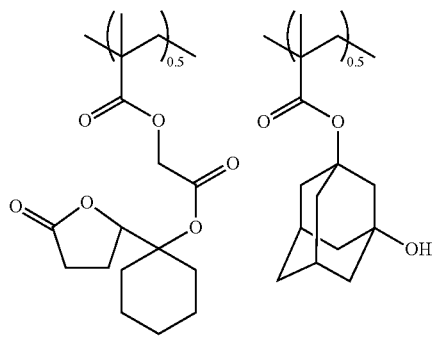

A round bottom flask having a volume of 100 mL, which was equipped with a nitrogen inlet, a stirrer, a reflux condenser and a thermometer, was charged with the whole of 5.9 g (25.0 mmoles) of 1-hydroxy-3-methacryloyloxyadamantane, 7.8 g (25.0 mmoles) of 4-(1'-methacryloyloxyacetoxycyclohexan-1'-yl)butanolide as obtained in the method of Example 5, 44 mL of methyl ethyl ketone and 0.66 g (4.0 mmoles) of azoisobutyronitrile under a nitrogen atmosphere, and the mixture was heated at 80° C. and polymerized for 4 hours. The obtained reaction solution was added dropwise in 1,000 mL of methanol at room temperature while stirring to obtain a white precipitate. The obtained precipitate was separated by filtration and dried in vacuo for 10 hours to obtain 3.6 g of desired Polymer Compound 3. Mw was 7,800, and Mw/Mn was 1.58.

Synthesis Example 9

Synthesis of Polymer Compound (Polymer Compound 4) Having the Following Structure

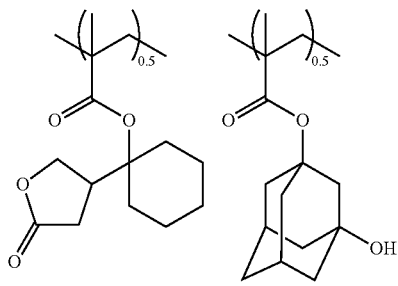

A round bottom flask having a volume of 100 mL, which was equipped with a nitrogen inlet, a stirrer, a reflux condenser and a thermometer, was charged with 5.9 g (25.0 mmoles) of 1-hydroxy-3-methacryloyloxyadamantane, 6.3 g (25.0 mmoles) of 3-(1'-methacryloyloxycyclohexan-1'-yl) butanolide as obtained in the method of Synthesis Example 4, 44 mL of methyl ethyl ketone and 0.66 g (4.0 mmoles) of azoisobutyronitrile under a nitrogen atmosphere, and the mixture was polymerized at 80° C. for 4 hours. The obtained reaction solution was added dropwise in 1,000 mL of methanol at room temperature while stirring to obtain a white precipitate. The obtained precipitate was separated by filtration and dried in vacuo for 10 hours to obtain 5.3 g of desired Polymer Compound 4. Mw was 7,300, and Mw/Mn was 1.72.

Synthesis Example 10

Synthesis of Polymer Compound (Polymer Compound 5) Having the Following Structure

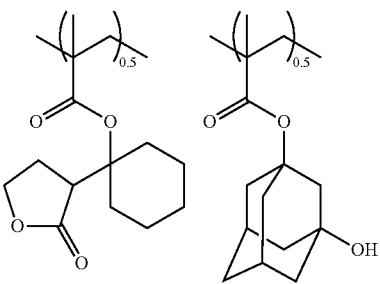

A round bottom flask having a volume of 100 mL, which was equipped with a nitrogen inlet, a stirrer, a reflux condenser and a thermometer, was charged with 5.9 g (25.0 mmoles) of 1-hydroxy-3-methacryloyloxyadamantane, 6.3 g (25.0 mmoles) of 2-(1'-methacryloyloxycyclohexan-1'-yl) butanolide as obtained in the method of Synthesis Example 5, 44 mL of methyl ethyl ketone and 0.66 g (4.0 mmoles) of azoisobutyronitrile under a nitrogen atmosphere, and the mixture was polymerized at 80° C. for 4 hours. The obtained reaction solution was added dropwise in 1,000 mL of methanol at room temperature while stirring to obtain a white precipitate. The obtained precipitate was separated by filtration and dried in vacuo for 10 hours to obtain 5.8 g of desired Polymer Compound 5. Mw was 7,500, and Mw/Mn was 1.63.

Synthesis Example 11

Synthesis of Polymer Compound (Polymer Compound 6) Having the Following Structure

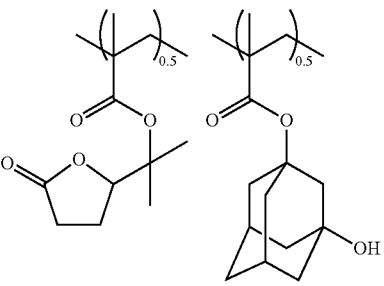

A round bottom flask having a volume of 100 mL, which was equipped with a nitrogen inlet, a stirrer, a reflux condenser and a thermometer, was charged with 5.9 g (25.0 mmoles) of 1-hydroxy-3-methacryloyloxyadamantane, 5.3 g (25.0 mmoles) of 4-(2'-methacryloyloxypropan-2'-yl)butanolide as obtained in the method of Synthesis Example 8, 44 mL of methyl ethyl ketone and 0.66 g (4.0 mmoles) of azoisobutyronitrile under a nitrogen atmosphere, and the mixture was polymerized at 80° C. for 4 hours. The obtained reaction solution was added dropwise in 100 mL of methanol at room temperature while stirring to obtain a white precipitate. The obtained precipitate was separated by filtration and dried in vacuo for 10 hours to obtain 5.8 g of desired Polymer Compound 6. Mw was 7,400, and Mw/Mn was 1.75.

Example 9

Synthesis of Polymer Compound (Polymer Compound 7) Having the Following Structure

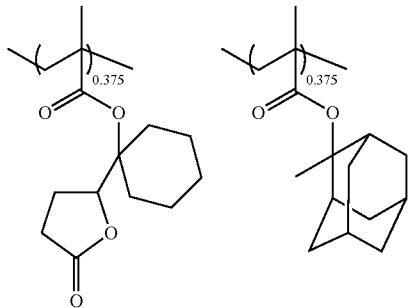

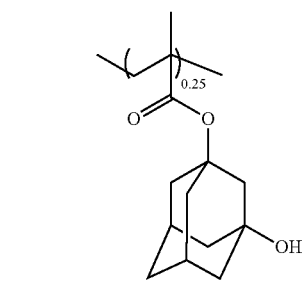

A round bottom flask having a volume of 100 mL, which was equipped with a nitrogen inlet, a stirrer, a reflux condenser and a thermometer, was charged with 4.39 g (18.7 mmoles) of 2-methacryloyloxy-2-methyladamantane, 2.96 g (12.5 mmoles) of 1-hydroxy-3-methacryloyloxyadamantane, 4.72 g (18.7 mmoles) of 4-(1'-methacryloyloxycyclohexan-1'-yl)butanolide as obtained in the method of Example 2, 44 mL of methyl ethyl ketone and 0.66 g (4.0 mmoles) of azoisobutyronitrile under a nitrogen atmosphere, and the mixture was polymerized at 80° C. for 4 hours. The obtained reaction solution was added dropwise in 100 mL of methanol at room temperature while stirring to obtain a white precipitate. The obtained precipitate was separated by filtration and dried in vacuo for 10 hours to obtain 5.25 g of desired Polymer Compound 7. Mw was 7,300, and Mw/Mn was 1.60.

Example 10

Synthesis of Polymer Compound (Polymer Compound 8) Having the Following Structure

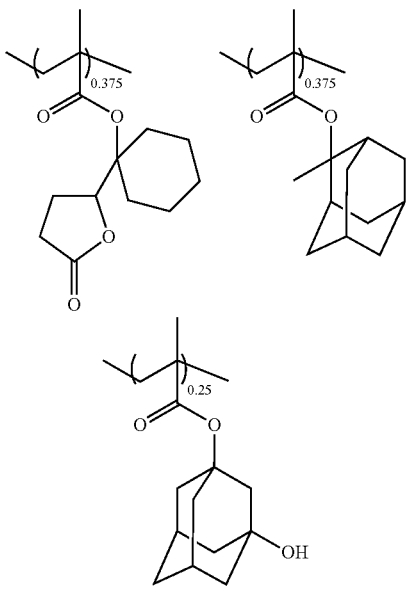

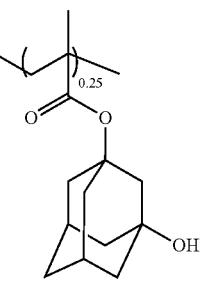

A round bottom flask having a volume of 100 mL, which was equipped with a nitrogen inlet, a stirrer, a reflux condenser and a thermometer, was charged with the whole of 4.39 g (18.7 mmoles) of 2-methacryloyloxy-2-methyladamantane, 2.96 g (12.5 mmoles) of 1-hydroxy-3-methacryloyloxyadamantane, 4.72 g (18.7 mmoles) of 4-(1'-methacryloyloxycyclohexan-1'-yl)butanolide as obtained in the method of Example 2, 44 mL of methyl ethyl ketone and 0.33 g (2.0 mmoles) of azoisobutyronitrile under a nitrogen atmosphere, and the mixture was polymerized at 80° C. for 6 hours. The obtained reaction solution was added dropwise in 1,000 mL of methanol at room temperature while stirring to obtain a white precipitate. The obtained precipitate was separated by filtration and dried in vacuo for 10 hours to obtain 5.45 g of desired Polymer Compound 8. Mw was 13,000, and Mw/Mn was 1.60.

Example 11

Synthesis of Polymer Compound (Polymer Compound 9) Having the Following Structure

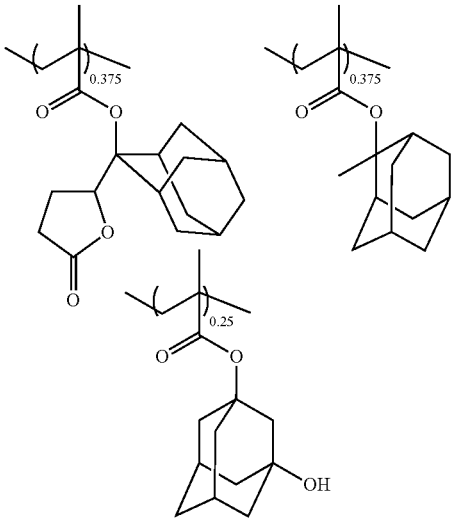

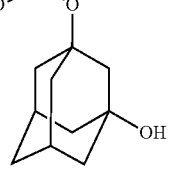

A round bottom flask having a volume of 100 mL, which was equipped with a nitrogen inlet, a stirrer, a reflux condenser and a thermometer, was charged with 4.39 g (18.7 mmoles) of 2-methacryloyloxy-2-methyladamantane, 2.96 g (12.5 mmoles) of 1-hydroxy-3-methacryloyloxyadamantane, 5.69 g (18.7 mmoles) of 4-(2'-methacryloyloxyadamantan-2'-yebutanolide as obtained in the method of Example 4, 44 mL of methyl ethyl ketone and 0.66 g (4.0 mmoles) of azoisobutyronitrile under a nitrogen atmosphere, and the mixture was polymerized at 80° C. for 4 hours. The obtained reaction solution was added dropwise in 1,000 mL of methanol at room temperature while stirring to obtain a white precipitate. The obtained precipitate was separated by filtration and dried in vacuo for 10 hours to obtain 5.30 g of desired Polymer Compound 9. Mw was 7,300, and Mw/Mn was 1.60.

Synthesis Example 12

Synthesis of Polymer Compound (Polymer Compound 10) Having the Following Structure

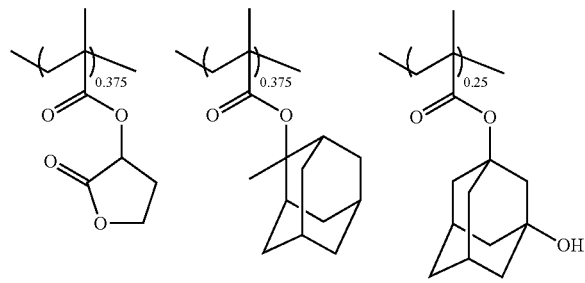

A round bottom flask having a volume of 100 mL, which was equipped with a nitrogen inlet, a stirrer, a reflux condenser and a thermometer, was charged with 4.39 g (18.7 mmoles) of 2-methacryloyloxy-2-methyladamantane, 2.96 g (12.5 mmoles) of 1-hydroxy-3-methacryloyloxyadamantane, 3.18 g (18.7 mmoles) of α-methacryloyloxy-γ-butyrolactone, 44 mL of methyl ethyl ketone and 0.66 g (4.0 mmoles) of azoisobutyronitrile under a nitrogen atmosphere, and the mixture was polymerized at 80° C. for 4 hours. The obtained reaction solution was added dropwise in 1,000 mL of methanol at room temperature while stirring to obtain a white precipitate. The obtained precipitate was separated by filtration and dried in vacuo for 10 hours to obtain 6.06 g of desired Polymer Compound 10. Mw was 10,000, and Mw/Mn was 1.50.

Examples 12 to 17 and Comparative Examples 1 to 4

Evaluation of Dissolution Rate and Maximum Amount of Swelling 100 parts by mass of each of Polymer Compounds 1 to 10 obtained in Examples 6 to 11 and Synthesis Examples 9 to 12 and 3 parts by mass of a photo acid generator (TPS-109, manufactured by Midori Kagaku Co., Ltd.) were dissolved in a mixed solvent of propylene glycol monomethyl ether acetate/ethyl lactate (1/1) (mass ratio) to prepare ten kinds of photoresist compositions each having a concentration of the polymer compound of 12% by mass. These photoresist compositions were each filtered using a filter (made of a tetrafluoroethylene resin (PTFE)) (0.2 μm) and then coated on a quartz substrate of 1 inch in size on the surface of which had been vacuum vapor deposited a gold electrode by a spin coating method, thereby forming a photosensitive film having a thickness of about 300 nm. These quartz substrates were each prebaked on a hot plate at a temperature of 130° C. for 90 seconds, subsequently exposed with an ArF excimer laser having a wavelength of 193 nm at an exposure amount of 100 mJ/cm$^2$ and then post-exposure baked at 130° C. for 90 seconds. These quartz substrates were each set in a quartz crystal microbalance device "RQCM" (manufactured by Maxtek, Inc.) and developed with a 2.38% by mass tetramethylammonium hydroxide aqueous solution for 120 seconds. A change in frequency of the quartz substrate during the development treatment was monitored with a lapse of time; and thereafter, the obtained change in frequency was reduced into a change in the film thickness, thereby defining a dissolution rate and a maximum amount of swelling.

<Evaluation of Pattern Shape>

100 parts by mass of each of Polymer Compounds 1 to 10 obtained in Examples 6 to 11 and Synthesis Examples 9 to 12, 3 parts by mass of a photo acid generator (TPS-109, manufactured by Midori Kagaku Co., Ltd.) and 0.25 parts by mass of triethanolamine were dissolved in a mixed solvent of propylene glycol monomethyl ether acetate/ethyl lactate (1/1) (mass ratio) to prepare ten kinds of photoresist compositions each having a concentration of the polymer compound of 12% by mass. These photoresist compositions were each filtered using a filter (made of a tetrafluoroethylene resin (PTFE)) (0.2 μm). On a silicon wafer having a diameter of 10 cm on which an antireflection film (base film) having a thickness of about 100 nm had been formed by coating a propylene glycol monomethyl ether acetate solution of a cresol/novolak resin (PS-6937, manufactured by Gun Ei Chemical Industry Co., Ltd.) in a concentration of 6% by mass by a spin coating method and baking on a hot plate at 200° C. for 90 seconds, each of the foregoing photoresist compositions was coated by a spin coating method to form a photoresist film having a thickness of about 300 nm. These were each prebaked on a hot plate at 130° C. for 90 seconds and then exposed with an ArF excimer laser having a wavelength of 193 nm by a double beam interference method. Subsequently, the exposed resist film was post-exposure baked at 130° C. for 90 seconds and then developed with a 2.38% by mass tetramethylammonium hydroxide aqueous solution for 60 seconds, thereby forming a 1:1 line-and-space pattern having a line width of 100 nm. The shape of the obtained resist pattern was observed by a scanning electron microscope (SEM), and a line width fluctuation (LWR) in a line width of 100 nm was also observed. As to LWR, a line width was detected at plural positions within a measuring monitor using a critical-dimension scanning electron microscope (SEM), and a 3σ value (σ: standard deviation) of that line width was defined as an index for LWR.

TABLE 1

| | Used polymer compound | Dissolution rate at development (nm/sec) | Maximum amount of swelling (nm) | LWR (nm) | Pattern shape |
|---|---|---|---|---|---|
| Example 12 | Polymer Compound 1 | 685 | 5 | 7.9 | Good |
| Example 13 | Polymer Compound 2 | 534 | 6 | 7.6 | Good |
| Example 14 | Polymer Compound 3 | 457 | 6 | 7.8 | Good |
| Example 15 | Polymer Compound 7 | 702 | 7 | 7.8 | Good |
| Example 16 | Polymer Compound 8 | 510 | 8 | 7.7 | Good |

TABLE 1-continued

| | Used polymer compound | Dissolution rate at development (nm/sec) | Maximum amount of swelling (nm) | LWR (nm) | Pattern shape |
|---|---|---|---|---|---|
| Example 17 | Polymer Compound 9 | 312 | 6 | 7.8 | Good |
| Comparative Example 1 | Polymer Compound 4 | 76 | 18 | 10.3 | Poor |
| Comparative Example 2 | Polymer Compound 5 | 85 | 21 | 10.7 | Poor |
| Comparative Example 3 | Polymer Compound 6 | 103 | 58 | 11.8 | Poor |
| Comparative Example 4 | Polymer Compound 10 | 60 | 40 | 12.3 | Poor |

It is understood from Table 1 that in the case of a photoresist composition using a polymer compound obtained by polymerizing one containing the polymerizable compound represented by the general formula (1) of the present invention (Examples 12 to 17), the dissolution rate in an alkaline developing solution to be used in the development process in manufacturing a photoresist pattern is very high, the maximum amount of swelling at the development is very small, and LWR is improved as compared with the case of a photoresist composition obtained by polymerizing one not containing the polymerizable compound represented by the general formula (1) of the present invention (Comparative Examples 1 to 4).

INDUSTRIAL APPLICABILITY

The tertiary alcohol derivative (1) and the polymer compound (4) of the present invention are useful as a raw material of a photoresist composition. Also, the photoresist composition of the present invention is useful as a photoresist composition for manufacturing an electronic device.

The invention claimed is:

1. A tertiary alcohol represented by formula (3):

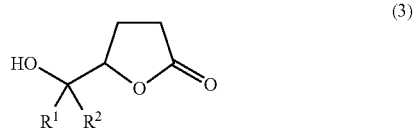

wherein $R^1$ and $R^2$ together form a ring comprising 3 to 10 carbon atoms and optionally comprising an oxygen atom.

2. The tertiary alcohol of claim 1, wherein the ring is selected from the group consisting of a cyclopropane ring, a cyclobutane ring, a cyclopentane ring, a cyclohexane ring, a cycloheptane ring, a camphor ring, a norbornane ring, an adamantane ring, a tetrahydrofuran ring and a tetrahydropyran ring.

3. The tertiary alcohol of claim 1, wherein the ring is a tetrahydrofuran ring or a tetrahydropyran ring.

4. The tertiary alcohol of claim 1, wherein the ring is a cyclopropane ring.

5. The tertiary alcohol of claim 1, wherein the ring is a cyclobutane ring.

6. The tertiary alcohol of claim 1, wherein the ring is a cyclopentane ring.

7. The tertiary alcohol of claim 1, wherein the ring is a cyclohexane ring.

8. The tertiary alcohol of claim 1, wherein the ring is a cycloheptane ring.

9. The tertiary alcohol of claim 1, wherein the ring is a camphor ring.

10. The tertiary alcohol of claim 1, wherein the ring is a norbornane ring.

11. The tertiary alcohol of claim 1, wherein the ring is an adamantane ring.

12. The tertiary alcohol of claim 1, wherein the ring is a tetrahydrofuran ring.

13. The tertiary alcohol of claim 1, wherein the ring is a tetrahydropyran ring.

* * * * *